(12) United States Patent
Nadeau et al.

(10) Patent No.: US 11,779,231 B2
(45) Date of Patent: Oct. 10, 2023

(54) MULTIPLE SOURCE-DETECTOR PAIR PHOTOPLETHYSMOGRAPHY (PPG) SENSOR

(71) Applicant: Fitbit, Inc., San Francisco, CA (US)

(72) Inventors: Kyle P. Nadeau, San Francisco, CA (US); Chris H. Sarantos, San Francisco, CA (US); Kevin Pu Weekly, San Leandro, CA (US); Javier L. Prieto, Oakland, CA (US); Peter W. Richards, San Francisco, CA (US); Paul Francis Stetson, Piedmont, CA (US); Aniket Sanjay Deshpande, Fremont, CA (US)

(73) Assignee: FITBIT, INC., San Francisco, CA (US)

( * ) Notice: Subject to any disclaimer, the term of this patent is extended or adjusted under 35 U.S.C. 154(b) by 145 days.

(21) Appl. No.: 17/366,235

(22) Filed: Jul. 2, 2021

(65) Prior Publication Data

US 2021/0330209 A1 Oct. 28, 2021

Related U.S. Application Data

(63) Continuation of application No. 15/948,970, filed on Apr. 9, 2018, now Pat. No. 11,051,706.

(60) Provisional application No. 62/482,997, filed on Apr. 7, 2017.

(51) Int. Cl.
*A61B 5/1455* (2006.01)
*A61B 5/024* (2006.01)
(Continued)

(52) U.S. Cl.
CPC ........ *A61B 5/02433* (2013.01); *A61B 5/0059* (2013.01); *A61B 5/02438* (2013.01);
(Continued)

(58) Field of Classification Search
CPC .. A61B 5/1455; A61B 5/14532; A61B 5/6852
See application file for complete search history.

(56) References Cited

U.S. PATENT DOCUMENTS

| | | | |
|---|---|---|---|
| 3,608,545 | A | 9/1971 | Novack et al. |
| 4,258,719 | A | 3/1981 | Lewyn |

(Continued)

FOREIGN PATENT DOCUMENTS

| | | | |
|---|---|---|---|
| CN | 1623175 A | 6/2005 | |
| CN | 1729933 | 8/2006 | |

(Continued)

OTHER PUBLICATIONS

"Health Touch™Plus User Guide," (2011) *Timex Group USA, Inc.*, 12pp.

(Continued)

*Primary Examiner* — Marjan Fardanesh
(74) *Attorney, Agent, or Firm* — Dority & Manning, P.A.

(57) ABSTRACT

Systems, devices, and methods for tracking one or more physiological metrics (e.g., heart rate, blood oxygen saturation, and the like) of a user are described. For example, one or more light sources and one or more light detectors may be positioned on a wearable device such that light can be emitted towards the user's skin and further such that light reflected back to the wearable device can be measured and used to generate values for the one or more physiological metrics.

20 Claims, 10 Drawing Sheets

(51) Int. Cl.
*A61B 5/00* (2006.01)
*A61B 5/11* (2006.01)

(52) U.S. Cl.
CPC .............. *A61B 5/11* (2013.01); *A61B 5/1455* (2013.01); *A61B 5/6824* (2013.01)

(56) References Cited

U.S. PATENT DOCUMENTS

| | | | |
|---|---|---|---|
| 4,367,752 A | 1/1983 | Jimenez et al. | |
| 4,771,792 A | 9/1988 | Seale | |
| 4,781,195 A | 11/1988 | Martin | |
| 4,846,183 A | 7/1989 | Martin | |
| 4,960,126 A | 10/1990 | Conlon et al. | |
| 5,036,856 A | 8/1991 | Thornton | |
| 5,101,831 A | 4/1992 | Koyama et al. | |
| 5,301,154 A | 4/1994 | Suga | |
| 5,318,597 A | 6/1994 | Hauck et al. | |
| 5,490,523 A | 2/1996 | Isaacson et al. | |
| 5,513,649 A | 5/1996 | Gevins et al. | |
| 5,734,625 A | 3/1998 | Kondo | |
| 5,738,104 A | 4/1998 | Lo et al. | |
| 5,830,137 A | 11/1998 | Scharf | |
| 5,954,644 A | 9/1999 | Dettling et al. | |
| 6,064,898 A * | 5/2000 | Aldrich | A61B 5/14532 600/316 |
| 6,076,015 A | 6/2000 | Hartley et al. | |
| 6,099,478 A | 8/2000 | Aoshima et al. | |
| 6,131,076 A | 10/2000 | Stephan et al. | |
| 6,241,684 B1 | 6/2001 | Amano et al. | |
| 6,289,230 B1 | 9/2001 | Chaiken et al. | |
| 6,307,576 B1 | 10/2001 | Rosenfeld | |
| 6,360,113 B1 | 3/2002 | Dettling | |
| 6,402,690 B1 | 6/2002 | Rhee et al. | |
| 6,418,394 B1 | 7/2002 | Puolakanaho et al. | |
| 6,583,369 B2 | 6/2003 | Montagnino et al. | |
| 6,585,622 B1 | 7/2003 | Shum et al. | |
| 6,731,967 B1 | 5/2004 | Turcott | |
| 6,882,955 B1 | 4/2005 | Ohlenbusch et al. | |
| 6,959,259 B2 | 10/2005 | Vock et al. | |
| 6,997,882 B1 | 2/2006 | Parker et al. | |
| 7,020,508 B2 | 3/2006 | Stivoric et al. | |
| 7,153,262 B2 | 12/2006 | Stivoric et al. | |
| 7,171,331 B2 | 1/2007 | Vock et al. | |
| 7,252,639 B2 | 8/2007 | Kimura et al. | |
| 7,285,090 B2 | 10/2007 | Stivoric et al. | |
| 7,334,472 B2 | 2/2008 | Seo et al. | |
| 7,539,532 B2 | 5/2009 | Tran | |
| 7,579,946 B2 | 8/2009 | Case, Jr. | |
| 7,720,306 B2 | 5/2010 | Gardiner et al. | |
| 7,890,153 B2 * | 2/2011 | Hoarau | A61B 5/062 600/323 |
| 7,909,768 B1 | 3/2011 | Turcott | |
| 7,993,276 B2 | 8/2011 | Nazarian et al. | |
| 8,040,758 B1 | 10/2011 | Dickinson | |
| 8,073,707 B2 | 12/2011 | Teller et al. | |
| 8,109,858 B2 | 2/2012 | Redmann | |
| 8,140,143 B2 | 3/2012 | Picard et al. | |
| 8,152,745 B2 | 4/2012 | Smith et al. | |
| 8,157,731 B2 | 4/2012 | Teller et al. | |
| 8,172,761 B1 | 5/2012 | Rulkov et al. | |
| 8,199,126 B1 | 6/2012 | Taubman | |
| 8,211,503 B2 | 7/2012 | Tsao et al. | |
| 8,346,328 B2 | 1/2013 | Mannheimer et al. | |
| 8,386,042 B2 | 2/2013 | Yudovsky et al. | |
| 8,398,546 B2 | 3/2013 | Pacione et al. | |
| 8,444,578 B2 | 5/2013 | Bourget et al. | |
| 8,446,275 B2 | 5/2013 | Utter, II | |
| 8,475,367 B1 | 7/2013 | Yuen et al. | |
| 8,579,827 B1 | 11/2013 | Rulkov et al. | |
| 8,641,612 B2 | 2/2014 | Teller et al. | |
| 8,684,900 B2 | 4/2014 | Tran | |
| 8,742,325 B1 | 6/2014 | Droz et al. | |
| 8,764,651 B2 | 7/2014 | Tran | |
| 8,792,981 B2 | 7/2014 | Yudovsky et al. | |
| 8,868,377 B2 | 10/2014 | Yuen et al. | |
| 8,909,543 B2 | 12/2014 | Trapper et al. | |
| 8,920,332 B2 | 12/2014 | Hong et al. | |
| 8,936,552 B2 | 1/2015 | Kateraas et al. | |
| 8,938,279 B1 | 1/2015 | Heaton, II et al. | |
| 8,945,017 B2 | 2/2015 | Venkatraman et al. | |
| 8,948,832 B2 | 2/2015 | Hong et al. | |
| 8,954,135 B2 | 2/2015 | Yuen et al. | |
| 8,956,303 B2 | 2/2015 | Hong et al. | |
| 8,961,413 B2 | 2/2015 | Teller et al. | |
| 8,998,815 B2 | 4/2015 | Venkatraman et al. | |
| 9,005,129 B2 | 4/2015 | Venkatraman et al. | |
| 9,014,790 B2 | 4/2015 | Richards et al. | |
| 9,031,812 B2 | 5/2015 | Roberts et al. | |
| 9,042,971 B2 | 5/2015 | Brumback et al. | |
| 9,044,149 B2 | 6/2015 | Richards et al. | |
| 9,044,150 B2 | 6/2015 | Brumback et al. | |
| 9,049,998 B2 | 6/2015 | Brumback et al. | |
| 9,089,760 B2 | 7/2015 | Trapper et al. | |
| 9,113,794 B2 | 8/2015 | Hong et al. | |
| 9,113,795 B2 | 8/2015 | Hong et al. | |
| 9,226,663 B2 | 1/2016 | Fei | |
| 9,237,855 B2 | 1/2016 | Hong et al. | |
| 9,282,902 B2 | 3/2016 | Richards et al. | |
| 9,307,917 B2 | 4/2016 | Hong et al. | |
| 9,314,166 B1 | 4/2016 | Brady et al. | |
| 9,314,197 B2 | 4/2016 | Eisen et al. | |
| 9,392,946 B1 | 7/2016 | Sarantos et al. | |
| 9,402,552 B2 | 8/2016 | Richards et al. | |
| 9,456,787 B2 | 10/2016 | Venkatraman et al. | |
| 9,662,053 B2 | 5/2017 | Richards et al. | |
| 9,775,548 B2 | 10/2017 | Sarantos et al. | |
| 10,178,973 B2 | 1/2019 | Venkatraman et al. | |
| 10,216,893 B2 | 2/2019 | Hong et al. | |
| 10,216,894 B2 | 2/2019 | Hong et al. | |
| 10,381,109 B2 | 8/2019 | Hong et al. | |
| 10,433,739 B2 | 10/2019 | Weekly et al. | |
| 10,512,407 B2 | 12/2019 | Richards et al. | |
| 10,568,525 B1 | 2/2020 | Wu et al. | |
| 2001/0044588 A1 | 11/2001 | Mault | |
| 2002/0077536 A1 | 6/2002 | Diab et al. | |
| 2002/0091329 A1 | 7/2002 | Heikkila et al. | |
| 2002/0139936 A1 | 10/2002 | Dumas | |
| 2003/0107487 A1 | 6/2003 | Man et al. | |
| 2003/0128867 A1 | 7/2003 | Bennett | |
| 2003/0163710 A1 | 8/2003 | Ortiz et al. | |
| 2003/0229276 A1 | 12/2003 | Sarussi et al. | |
| 2004/0171969 A1 | 9/2004 | Socci et al. | |
| 2004/0190085 A1 | 9/2004 | Silverbrook et al. | |
| 2004/0236227 A1 | 11/2004 | Gueissaz | |
| 2005/0020927 A1 | 1/2005 | Blondeau et al. | |
| 2005/0054940 A1 | 3/2005 | Almen | |
| 2005/0245793 A1 | 11/2005 | Hilton et al. | |
| 2005/0253047 A1 | 11/2005 | Maegawa et al. | |
| 2006/0052727 A1 | 3/2006 | Palestrant | |
| 2006/0195020 A1 | 8/2006 | Martin et al. | |
| 2007/0213020 A1 | 9/2007 | Novae | |
| 2007/0219059 A1 | 9/2007 | Schwartz et al. | |
| 2007/0265533 A1 | 11/2007 | Tran | |
| 2008/0039729 A1 | 2/2008 | Cho et al. | |
| 2008/0097221 A1 | 4/2008 | Florian | |
| 2008/0214360 A1 | 9/2008 | Stirling et al. | |
| 2008/0214903 A1 | 9/2008 | Orbach | |
| 2008/0287751 A1 | 11/2008 | Stivoric et al. | |
| 2009/0012433 A1 | 1/2009 | Femstrom et al. | |
| 2009/0132197 A1 | 5/2009 | Rubin et al. | |
| 2009/0143655 A1 | 6/2009 | Shani | |
| 2009/0163783 A1 | 6/2009 | Mannheimer et al. | |
| 2009/0216499 A1 | 8/2009 | Tobola et al. | |
| 2009/0292332 A1 | 11/2009 | Li et al. | |
| 2009/0318779 A1 | 12/2009 | Tran | |
| 2010/0026995 A1 | 2/2010 | Merritt et al. | |
| 2010/0063365 A1 | 3/2010 | Pisani et al. | |
| 2010/0079291 A1 | 4/2010 | Kroll et al. | |
| 2010/0106044 A1 | 4/2010 | Linderman | |
| 2010/0113948 A1 | 5/2010 | Yang et al. | |
| 2010/0152600 A1 | 6/2010 | Droitcour et al. | |
| 2010/0204550 A1 | 8/2010 | Heneghan et al. | |
| 2010/0240972 A1 | 9/2010 | Neal | |
| 2010/0249633 A1 | 9/2010 | Droitcour et al. | |

(56) References Cited

U.S. PATENT DOCUMENTS

| | | |
|---|---|---|
| 2010/0274100 A1 | 10/2010 | Behar et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | Mccombie et al. |
| 2010/0298661 A1 | 11/2010 | Mccombie et al. |
| 2010/0331145 A1 | 12/2010 | Lakovic et al. |
| 2010/0331657 A1 | 12/2010 | Mensinger et al. |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0112442 A1 | 5/2011 | Meger et al. |
| 2011/0118621 A1 | 5/2011 | Chu |
| 2011/0237911 A1 | 9/2011 | Lamego et al. |
| 2011/0237912 A1 | 9/2011 | Couronne et al. |
| 2011/0263950 A1 | 10/2011 | Larson et al. |
| 2011/0276304 A1 | 11/2011 | Yin et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0140233 A1 | 6/2012 | Rockwell et al. |
| 2012/0143067 A1 | 6/2012 | Watson et al. |
| 2012/0150052 A1 | 6/2012 | Buccheim et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0253486 A1 | 10/2012 | Niemimaki |
| 2012/0255875 A1 | 10/2012 | Vicente et al. |
| 2012/0271180 A1 | 10/2012 | Ren et al. |
| 2012/0274508 A1 | 11/2012 | Brown et al. |
| 2012/0316471 A1 | 12/2012 | Rahman et al. |
| 2013/0009779 A1 | 1/2013 | Wittling et al. |
| 2013/0053661 A1 | 2/2013 | Alberth et al. |
| 2013/0073254 A1 | 3/2013 | Yuen et al. |
| 2013/0073255 A1 | 3/2013 | Yuen et al. |
| 2013/0077823 A1 | 3/2013 | Mestha et al. |
| 2013/0077826 A1 | 3/2013 | Cowperthwaite et al. |
| 2013/0079607 A1 | 3/2013 | Gareau et al. |
| 2013/0080113 A1 | 3/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0173171 A1 | 7/2013 | Drysdale et al. |
| 2013/0191034 A1 | 7/2013 | Weast et al. |
| 2013/0211265 A1 | 8/2013 | Bedingham et al. |
| 2013/0218053 A1 | 8/2013 | Kaiser et al. |
| 2013/0245436 A1 | 9/2013 | Tupin, Jr. et al. |
| 2013/0261415 A1 | 10/2013 | Ashe et al. |
| 2014/0039284 A1 | 2/2014 | Niwayama et al. |
| 2014/0073486 A1 | 3/2014 | Ahmed et al. |
| 2014/0074431 A1 | 3/2014 | Modi |
| 2014/0099614 A1 | 4/2014 | Hu et al. |
| 2014/0107493 A1 | 4/2014 | Yuen et al. |
| 2014/0135612 A1 | 5/2014 | Yuen et al. |
| 2014/0135631 A1 | 5/2014 | Brumback et al. |
| 2014/0142403 A1 | 5/2014 | Brumback et al. |
| 2014/0180022 A1 | 6/2014 | Stivoric et al. |
| 2014/0228649 A1 | 8/2014 | Rayner |
| 2014/0241626 A1 | 8/2014 | Sull et al. |
| 2014/0275821 A1 | 9/2014 | Beckman |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0303523 A1 | 10/2014 | Hong et al. |
| 2014/0378786 A1 | 12/2014 | Hong et al. |
| 2014/0378787 A1 | 12/2014 | Brumback et al. |
| 2014/0378844 A1 | 12/2014 | Fei |
| 2014/0378872 A1 | 12/2014 | Hong et al. |
| 2015/0025393 A1 | 1/2015 | Hong et al. |
| 2015/0025394 A1 | 1/2015 | Hong et al. |
| 2015/0026647 A1 | 1/2015 | Park et al. |
| 2015/0173631 A1 | 6/2015 | Richards et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230743 A1 | 8/2015 | Silveira et al. |
| 2015/0230761 A1 | 8/2015 | Brumback et al. |
| 2015/0282713 A1 | 10/2015 | Fei |
| 2015/0351646 A1 | 12/2015 | Cervini |
| 2015/0366469 A1 | 12/2015 | Harris et al. |
| 2015/0366504 A1 | 12/2015 | Connor et al. |
| 2016/0029968 A1 | 2/2016 | Lerner et al. |
| 2016/0034634 A9 | 2/2016 | Hong et al. |
| 2016/0058309 A1 | 3/2016 | Han |
| 2016/0058312 A1 | 3/2016 | Han et al. |
| 2016/0113585 A1 | 4/2016 | Uedaira et al. |
| 2016/0183818 A1 | 6/2016 | Richards et al. |
| 2016/0302706 A1 | 10/2016 | Richards et al. |
| 2016/0345881 A1 | 12/2016 | Sarantos et al. |
| 2017/0020659 A1 | 1/2017 | Hyde et al. |
| 2017/0027523 A1 | 2/2017 | Venkatraman et al. |
| 2017/0164848 A1 | 6/2017 | Nadeau et al. |
| 2017/0311825 A1 | 11/2017 | Weekly et al. |
| 2018/0108802 A1 | 4/2018 | Chen |
| 2018/0310846 A1 | 11/2018 | Lin |
| 2019/0082985 A1 | 3/2019 | Hong et al. |
| 2019/0385708 A1 | 12/2019 | Hong et al. |
| 2020/0138309 A1 | 5/2020 | Weekly et al. |

FOREIGN PATENT DOCUMENTS

| | | |
|---|---|---|
| CN | 101039617 A | 9/2007 |
| CN | 100362963 C | 1/2008 |
| CN | 101615098 A | 12/2009 |
| CN | 101730503 | 6/2010 |
| CN | 101742981 A | 6/2010 |
| CN | 101940476 A | 1/2011 |
| CN | 102008811 A | 4/2011 |
| CN | 202069586 U | 12/2011 |
| CN | 102389313 A | 3/2012 |
| CN | 102551686 A | 7/2012 |
| CN | 102750015 A | 10/2012 |
| CN | 102781310 A | 11/2012 |
| CN | 103093420 A | 5/2013 |
| CN | 104379055 A | 2/2015 |
| EP | 1297784 A1 | 4/2003 |
| EP | 1586353 A1 | 10/2005 |
| EP | 1721237 B1 | 8/2012 |
| JP | 2010169410 A | 5/2010 |
| WO | WO2006/044677 A1 | 4/2006 |
| WO | WO2012/170586 A2 | 12/2012 |
| WO | WO2012/170924 A2 | 12/2012 |
| WO | WO2012/171032 A2 | 12/2012 |
| WO | WO2014/091424 A2 | 6/2014 |
| WO | WO2014/091424 A3 | 6/2014 |
| WO | WO2015/127067 A1 | 8/2015 |
| WO | WO2016/003269 A1 | 1/2016 |
| WO | WO2017190051 | 11/2017 |

OTHER PUBLICATIONS

"New Lifestyles, NL-800 Activity Monitor, User's guide & record book," (2005), New Lifestyles, Inc., 37pp.

"Solo 915, Heart Rate+ Calorie Monitor," (2009) *Sportline@*, [retrieved on Oct. 15, 2010 at www.sportline.com] 25pp.

"StepWatch Step Activity Monitor, U.S. Pat. No. 5,485,402," (2001) StepWatch™, *Prosthetics Research Study*,7pp.

(56) References Cited

OTHER PUBLICATIONS

"UP3™, The world's most advanced tracker," (Oct. 14, 2015) *Jawbone*, 10pp.
"UP4™, A fitness tracker so advanced it pays," (Oct. 14, 2015) *Jawbone*, 12pp.
"User's Guide, MIO Drive+ Petite," User's guide and how-to videos available at www.mioglobal.com, 3pp.
"Withings pulse, Quick Installation Guide" (Jul. 24, 2013) Withings Pulse QIG, v1.3, withings.com/pulse, 16 pages.
Chinese First Office Action dated Aug. 3, 2016 issued in Application No. CN 201410243169.X.
Chinese First Office Action dated Aug. 7, 2015 issued in Application No. CN 201410243180.6.
Chinese First Office Action dated Jan. 14, 2019 issued in Application No. CN 201510117698.X.
Chinese First Office Action dated Jan. 22, 2020, issued in Application No. CN 201780033558.1.
Chinese First Office Action dated Jul. 13, 2017 issued in Application No. CN201610621114.7.
Chinese First Office Action dated Mar. 22, 2018 issued in Application No. CN 201610284612.7.
Chinese First Office Action dated Mar. 3, 2017 issued in Application No. CN 201610622453.7.
Chinese First Office Action dated May 13, 2020, issued in Application No. CN 201610377864.4.
Chinese First Office Action dated Sep. 2, 2016 issued in Application No. CN 201510745382.5.
Chinese First Office Action dated Sep. 26, 2016 issued in Application No. CN 201410243178.9.
Chinese First Office Action dated Sep. 27, 2016 issued in Application No. CN 201410018701.8.
Chinese Fourth Office Action dated Jun. 1, 2018 issued in Application No. CN 201610622453.7.
Chinese Second Office Action dated Apr. 9, 2018 issued in Application No. CN 201610621114.7.
Chinese Second Office Action dated Jun. 13, 2017 issued in Application No. CN 201410018701.8.
Chinese Second Office Action dated Jun. 15, 2017 issued in Application No. CN 201410243178.9.
Chinese Second Office Action dated Jun. 21, 2019 issued in Application No. CN 201510117698.X.
Chinese Second Office Action dated Mar. 22, 2017 issued in Application No. CN 201510745382.5.
Chinese Second Office Action dated Mar. 27, 2017 issued in Application No. CN 201410243169.X.
Chinese Second Office Action dated Nov. 6, 2018 issued in Application No. CN 201610284612.7.
Chinese Second Office Action dated Sep. 19, 2017 issued in Application No. CN 201610622453.7.
Chinese Third Office Action dated Jan. 24, 2018 issued in Application No. CN 201610622453.7.
Chinese Third Office Action dated Sep. 14, 2018 issued in Application No. CN 201610621114.7.
Chinese Third Office Action dated Sep. 28, 2017 issued in Application No. CN 201410243169.X.
Cooper, Daniel (Aug. 16, 2013) *Withings Pulse review*, http://www.engadget.com/2013/08/16/withings-pulse-revew/, 8 pages.
Czamul, Pawel (Jun. 6-8, 2013) "Design of a Distributed System using Mobile Devices and Workflow Management for Measurement and Control of a Smart Home and Health," Sopot, Poland, *IEEE*, pp. 184-192, 10pp.
Dunn et al. (2007) "A Novel Ring Shaped Photodiode for Reflectance Pulse Oximetry in Wireless Applications," *IEEE Sensors Conference*, pp. 596-599.
European Extended Search Report dated Oct. 25, 2016 issued in Application No. EP 16168661.3.
European Extended Search Report dated Sep. 9, 2019, issued in Application No. EP 17790575.9.
European Office Action dated Mar. 19, 2019 issued in Application No. EP 16168661.3.

Gasparrini et al. (2013) "Evaluation and Possible Improvements of the ANT Protocol for Home Heart Monitoring Applications," *IEEE*, 978-1-4673-2874-6/13, 7pp.
Graser et al. (2007) "Effects of Placement, Attachment, and Weight Classification on Pedometer Accuracy," *Journal of Physical Activity and Health*, 4(4):359-369, 13pp.
Horvath et al. (2007) "The effect of pedometer position and normal gait asymmetryon step count accuracy," *Avvl. Phvsiol. Nutr. Metab.*, 32:409-415, 800.
International Search Report and Written Opinion for PCT/US2017/030190—ISA/US—dated Jul. 7, 2017.
Kim, D. et al. A Linear Transformation Approach for Estimating Pulse Arrival Time. Journal of Applied Mathematics. vol. 2012. Jan. 20, 2012. [Retrieve Jun. 19, 2017]. Retrieved from internet: <https://www.emis.de/journals/HOA/JAMNolume2012/643653,pdf> pp. 1-12.
LIFETRNR, User Manual (2003, specific date unknown), NB new balance®, ImplusFootcare, LLC, 3 pages.
Litigation Document—"Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 337-TA-973)[in the Matter of Certain Wearable Activity Tracking Devices, Systems, and Components Thereof].
Litigation Document—"Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [in the Matter of Certain Wearable Activity Tracking Devices, Systems, and Components Thereof].
Litigation Document—"Declaration of Majid Sarrafzadeh in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [in the Matter of Certain Wearable Activity Tracking Devices, Systems, and Components Thereof] 2.
Litigation Document—"Grimes Declaration in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [in the Matter of Certain Wearable Activity Tracking Devices, Systems, and Components Thereof].
Litigation Document—"Kiaei Declaration in Support of Complainant's SupplementalBrief Regarding Construction of "Operating the Heart Rate Monitor in a Worn Detection Mode" under 35 U.S.C. § 1 12(f)," filed Apr. 29, 2016, in United States International Trade Commission, Washington, D.C. (Investigation No. 37-TA-973) [in the Matter of Certain Wearable Activity Tracking Devices, Systems, and Components Thereof].
Litigation Document—"Memorandum in Support of Respondents' Motion for Summary Determination that the Asserted Patents are Directed to Ineligible Subject Matter under 35 U.S.C. § 101," filed May 23, 2016, in United States International Trade Commission, Washington, D.C. (Investigation No. 337-TA-973) (44325007v1/014972) [in the Matter of Certain Wearable Activity Tracking Devices, Systems, and Components Thereof].
Litigation Document—"Notice of Commission Determination to Review an Initial Determination Granting Respondents' Motion for Summary Determination that Certain Asserted Claims are Directed to Ineligible Subject Matter under 35 U.S.C. § 101; and on Review to Remand the Investigation to the Presiding Administrative LawJudge," issued Sep. 7, 2016, in United States International Trade Commission, Washington, D.C. (Investigation No. 337-TA-973) [in the Matter of Certain Wearable Activity Tracking Devices, Systems, and Components Thereof].
Litigation Document—"Order No. 24: Initial Determination Granting Respondents' Motion for Summary Determination of Invalidity under 35 U.S.C. § 101 with respect to all Three Asserted Patents and Terminating the Investigation in its Entirety," filed Jul. 19, 2016, in United States International Trade Commission, Washington, D.C. (Investigation No. 337-TA-973) [in the Matter of Certain Wearable Activity Tracking Devices, Systems, and Components Thereof].

(56) References Cited

OTHER PUBLICATIONS

Litigation Document—"Report on the Filing or Determination of an Action Regarding a Patent or Trademark," filed Sep. 3, 2015, in U.S. District Court ofDelaware.
Litigation Document—"Report on the Filing or Determination of an Action Regarding a Patent or Trademark," filed Oct. 29, 2015, in U.S. District Court of Delaware [Re: U.S. Pat. No. 8,868,377, 8,920,332, and 9,089,760].
Litigation Document—"Respondents' Opposition to Complainant's Petition for Review of the Initial Determination Granting Summary Determination that the Asserted Patents are Directed to Ineligible Subject Matter under 35 U.S.C. § 101," filed Aug. 8, 2016, in United States International Trade Commission, Washington, D.C. (Investigation No. 337-TA-973) (4446833v1/014972) [in the Matter of Certain Wearable Activity Tracking Devices, Systems, and Components Thereof].
Litigation Document—"Summary Pursuant to 19 C.F.R. § 210.43(b)(2) of Complainant's Petition for Review of the Initial Determination Granting SummaryDetermination that the Asserted Patents are Directed to Ineligible Subject Matter under 35 U.S.C. § 101," filed Aug. 1, 2016, in United States International Trade Commission, Washington, D.C. (Investigation No. 337-TA-973) [in the Matter of Certain Wearable Activity Tracking Devices, Systems, and Components Thereof].
Litigation Document—"Complaint for Patent Infringement," filed Oct. 29, 2015, in U.S. District Court of Delaware [Re:U.S. Pat. No. 8,868,377, 8,920,332, and 9,089,760].
Litigation Document—"Complaint for Patent Infringement," filed Sep. 3, 2015, in U.S. District Court of Delaware.
Litigation Document—"Plaintiffs Original Complaint for Patent Infringement," filedJan. 4, 2016, in U.S. District Court for the Eastern District of North Carolina [Re: U.S. Pat. No. 8,923,941, 8,886,269, 8,929,965 and 8,989,830], 11 pages.
Rabinovich, Roberto A., and Louvaris, Zafeiris et al. (Feb. 8, 2013) "Validityof Physical Activity Monitors During Daily Life in Patients With COPD," *ERJ Express, European Respiratory Society*, 28pp.
Rainmaker, (Jun. 25, 2012, updated Feb 16, 2013) "Garmin Swim watch In-DepthReview," [retrieved on Sep. 9, 2013 at http://www.dcrainmaker.com/2012/06/garmin-swim-in-depth-review.html, 38 pp.
Unpublished U.S. Appl. No. 14/214,655, filed Mar. 14, 2014.
Unpublished U.S. Appl. No. 15/494,257, filed Apr. 21, 2017.
Unpublished U.S. Appl. No. 16/592,599, filed Oct. 3, 2019.
Unpublished U.S. Appl. No. 16/798,257, filed Feb. 21, 2020.
US Examiner's Answer to Appeal Brief before the Patent Trial and Appeal Board [in response to the appeal brief filed Sep. 12, 2017 appealing from the Office action dated Jan. 3, 2017], dated Nov. 30, 2017, issued in U.S. Appl. No. 14/216,743.
US Examiner's Answer to Appeal Brief before the Patent Trial and Appeal Board [in response to the appeal brief filed Dec. 9, 2016 appealing from the Office action dated May 13, 2016], dated Jan. 23, 2017, issued in U.S. Appl. No. 14/481,020.
US Examiner's Answer to the Appeal Brief before the Patent Trial and Appeal Board [in response to the appeal brief filed Jul. 11, 2017 appealing from the Office action dated Jan. 9, 2017], dated Aug. 24, 2017, issued in U.S. Appl. No. 14/250,256.
U.S. Final Office Action dated Aug. 1, 2017, issued in U.S. Appl. No. 15/370,303.
U.S. Final Office Action dated Aug. 3, 2017, issued in U.S. Appl. No. 14/599,039.
U.S. Final Office Action dated Feb. 7, 2017, issued in U.S. Appl. No. 15/192,447.
U.S. Final Office Action dated Jul. 25, 2018, issued in U.S. Appl. No. 15/370,303.
U.S. Final Office Action, dated Apr. 15, 2015, issued in U.S. Appl. No. 14/295,076.
U.S. Final Office Action, dated Apr. 8, 2015, issued in U.S. Appl. No. 14/216,743.
U.S. Final Office Action, dated Aug. 9, 2017, issued in U.S. Appl. No. 14/673,634.
U.S. Final Office Action, dated Dec. 19, 2014, issued in U.S. Appl. No. 14/481,762.
U.S. Final Office Action, dated Feb. 21, 2019, issued in U.S. Appl. No. 14/640,281.
U.S. Final Office Action, dated Feb. 26, 2019, issued in U.S Appl. No. 14/696,256.
U.S. Final Office Action, dated Feb. 8, 2016, issued in U.S. Appl. No. 14/216,743.
U.S. Final Office Action, dated Jul. 7, 2015, issued in U.S. Appl. No. 14/481,020.
U.S. Final Office Action, dated Jun. 29, 2016, issued in U.S. Appl. No. 14/250,256.
U.S. Final Office Action, dated May 11, 2015, issued in U.S. Appl. No. 14/507,184.
U.S. Final Office Action, dated May 13, 2016, issued in U.S. Appl. No. 14/481,020.
U.S. Final Office Action, dated May 4, 2017, issued in U.S. Appl. No. 14/640,281.
U.S. Final Office Action, dated Nov. 12, 2015, issued in U.S. Appl. No. 14/640,281.
U.S. Final Office Action, dated Nov. 21, 2014, issued in U.S. Appl. No. 14/250,256.
U.S. Final Office Action, dated Nov. 4, 2015, issued in U.S. Appl. No. 14/673,634.
U.S. Final Office Action, dated Nov. 5, 2015, issued in U.S. Appl. No. 14/481,762.
U.S. Final Office Action, dated Oct. 19, 2016, issued in U.S. Appl. No. 14/481,762.
U.S. Final Office Action, dated Oct. 23, 2015, issued in U.S. Appl. No. 14/250,256.
U.S. Notice of Allowance (Corrected Notice of Allowability), dated Oct. 14, 2014,issued in U.S. Appl. No. 14/292,669.
U.S. Notice of Allowance (Corrected Notice of Allowability), dated Dec. 31, 2014, issued in U.S. Appl. No. 14/292,66.
U.S. Notice of Allowance (Corrected Notice of Allowability), dated Dec. 31, 2014, issued in U.S. Appl. No. 14/295,158.
U.S. Notice of Allowance (Corrected Notice of Allowability), dated Dec. 18, 2015, issued in U.S. Appl. No. 14/507,184.
U.S. Notice of Allowance (Corrected Notice of Allowability), dated Mar. 21, 2016, issued in U.S. Appl. No. 14/673,630.
U.S. Notice of Allowance (Corrected Notice of Allowability), dated Jul. 16, 2015, issued in U.S. Appl. No. 14/507,173.
U.S. Notice of Allowance (Corrected Notice of Allowability), dated Mar. 5, 2015, issued in U.S. Appl. No. 14/292,673.
U.S. Notice of Allowance (Corrected Notice of Allowability), dated Mar. 11, 2015, issued in U.S. Appl. No. 14/295,059.
U.S. Notice of Allowance (Corrected Notice of Allowability), dated Jan. 5, 2015, issued in U.S. Appl. No. 14/295,122.
U.S. Notice of Allowance (Corrected Notice of Allowability), dated May 14, 2015, issued in U.S. Appl. No. 14/154,019.
U.S. Notice of Allowance (Corrected Notice of Allowability), dated May 6, 2015, issued in U.S. Appl. No. 14/484,104.
U.S. Notice of Allowance dated Oct. 14, 2014 issued in U.S. Appl. No. 14/295,144.
U.S. Notice of Allowance dated May 24, 2017, issued in U.S. Appl. No. 15/192,447.
U.S. Notice of Allowance, dated Apr. 14, 2015, issued in U.S. Appl. No. 14/295,161.
U.S. Notice of Allowance, dated Apr. 15, 2016, issued in U.S. Appl. No. 14/954,753.
U.S. Notice of Allowance, dated Apr. 17, 2015, issued in U.S. Appl. No. 14/507,173.
U.S. Notice of Allowance, dated Aug. 11, 2015, issued in U.S. Appl. No. 14/507,184.
U.S. Notice of Allowance, dated Aug. 2, 2019, issued in U.S. Appl. No. 14/640,281.
U.S. Notice of Allowance, dated Aug. 29, 2018, issued in U.S. Appl. No. 15/246,387.
U.S. Notice of Allowance, dated Dec. 17, 2018, issued in U.S. Appl. No. 14/216,743.
U.S. Notice of Allowance, dated Dec. 3, 2014, issued in U.S. Appl. No. 14/295,144.

(56) References Cited

OTHER PUBLICATIONS

U.S. Notice of Allowance, dated Dec. 8, 2014, issued in U.S. Appl. No. 14/292,673.
U.S. Notice of Allowance, dated Feb. 6, 2015, issued in U.S. Appl. No. 14/290,884.
U.S. Notice of Allowance, dated Feb. 9, 2015, issued in U.S. Appl. No. 14/292,844.
U.S. Notice of Allowance, dated Jan. 21, 2015, issued in U.S. Appl. No. 14/154,009.
U.S. Notice of Allowance, dated Jan. 23, 2017, issued in U.S. Appl. No. 15/195,911.
U.S. Notice of Allowance, dated Jan. 28, 2015, issued in U.S. Appl. No. 14/295,059.
U.S. Notice of Allowance, dated Jul. 27, 2015, issued in U.S. Appl. No. 14/693,710.
U.S. Notice of Allowance, dated Jul. 28, 2015, issued in U.S. Appl. No. 14/295,161.
U.S. Notice of Allowance, dated Jun. 14, 2019, issued in U.S. Appl. No. 15/582,240.
U.S. Notice of Allowance, dated Mar. 19, 2015, issued in U.S. Appl. No. 14/484,104.
U.S. Notice of Allowance, dated Mar. 20, 2015, issued in U.S. Appl. No. 14/154,019.
U.S. Notice of Allowance, dated Mar. 29, 2019, issued in U.S. Appl. No. 14/250,256.
U.S. Notice of Allowance, dated Mar. 8, 2016, issued in U.S. Appl. No. 14/724,750.
U.S. Notice of Allowance, dated May 24, 2016, issued in U.S. Appl. No. 14/295,076.
U.S. Notice of Allowance, dated Nov. 19, 2014, issued in U.S. Appl. No. 13/924,784.
U.S. Notice of Allowance, dated Nov. 24, 2014, issued in U.S. Appl. No. 14/295,122.
U.S. Notice of Allowance, dated Nov. 25, 2015, issued in U.S. Appl. No. 14/673,630.
U.S. Notice of Allowance, dated Nov. 29, 2018, issued in U.S. Appl. No. 14/481,020.
U.S. Notice of Allowance, dated Sep. 20, 2019, issued in U.S. Appl. No. 15/376,542.
U.S. Notice of Allowance, dated Sep. 23, 2014, issued in U.S. Appl. No. 14/292,669.
U.S. Notice of Allowance, dated Sep. 26, 2014, issued in U.S. Appl. No. 14/295,158.
U.S. Office Action dated Dec. 22, 2016, issued in U.S. Appl. No. 14/599,039.
U.S. Office Action dated Jan. 11, 2018, issued in U.S. Appl. No. 15/370,303.
U.S. Office Action dated Mar. 15, 2017, issued in U.S. Appl. No. 15/370,303.
U.S. Office Action dated May 24, 2019, issued in U.S. Appl. No. 15/370,303.
U.S. Office Action dated Sep. 8, 2016, issued in U.S. Appl. No. 15/192,447.
U.S. Office Action, dated Apr. 12, 2017, issued in U.S. Appl. No. 14/481,762.
U.S. Office Action, dated Aug. 22, 2014, issued in U.S. Appl. No. 14/250,256.
U.S. Office Action, dated Aug. 4, 2014, issued in U.S. Appl. No. 13/924,784.
U.S. Office Action, dated Aug. 5, 2014, issued in U.S. Appl. No. 14/292,673.
U.S. Office Action, dated Dec. 10, 2014, issued in U.S. Appl. No. 14/484,104.
U.S. Office Action, dated Dec. 24, 2014, issued in U.S. Appl. No. 14/295,076.
U.S. Office Action, dated Dec. 4, 2014, issued in U.S. Appl. No. 14/216,743.
U.S. Office Action, dated Feb. 19, 2020, issued in U.S. Appl. No. 14/696,256.
U.S. Office Action, dated Feb. 9, 2017, issued in U.S. Appl. No. 14/673,634.
U.S. Office Action, dated Jan. 12, 2018, issued in U.S. Appl. No. 15/246,387.
U.S. Office Action, dated Jan. 13, 2017, issued in U.S. Appl. No. 14/216,743.
U.S. Office Action, dated Jan. 23, 2015, issued in U.S. Appl. No. 14/507,184.
U.S. Office Action, dated Jan. 26, 2015, issued in U.S. Appl. No. 14/295,161.
U.S. Office Action, dated Jan. 27, 2015, issued in U.S. Appl. No. 14/507,173.
U.S. Office Action, dated Jan. 9, 2017, issued in U.S. Appl. No. 14/250,256.
U.S. Office Action, dated Jul. 13, 2016, issued in U.S. Appl. No. 14/673,634.
U.S. Office Action, dated Jul. 24, 2018, issued in U.S. Appl. No. 14/696,256.
U.S. Office Action, dated Jul. 31, 2014, issued in U.S. Appl. No. 14/295,122.
U.S. Office Action, dated Jul. 6, 2015, issued in U.S. Appl. No. 14/640,281.
U.S. Office Action, dated Jul. 7, 2015, issued in U.S. Appl. No. 14/481,762.
U.S. Office Action, dated Jul. 8, 2015, issued in U.S. Appl. No. 14/250,256.
U.S. Office Action, dated Jun. 22, 2015, issued in U.S. Appl. No. 14/693,710.
U.S. Office Action, dated Jun. 29, 2018, issued in U.S. Appl. No. 14/640,281.
U.S. Office Action, dated Jun. 8, 2015, issued in U.S. Appl. No. 14/673,634.
U.S. Office Action, dated Mar. 11, 2019, issued in U.S. Appl. No. 15/582,240.
U.S. Office Action, dated Mar. 12, 2015, issued in U.S. Appl. No. 14/481,020.
U.S. Office Action, dated Mar. 14, 2014, issued in U.S. Appl. No. 14/154,009.
U.S. Office Action, dated Mar. 17, 2016, issued in U.S. Appl. No. 14/250,256.
U.S. Office Action, dated Mar. 27, 2018, issued in U.S. Appl. No. 14/673,634.
U.S. Office Action, dated May 11, 2015, issued in U.S. Appl. No. 14/673,630.
U.S. Office Action, dated May 11, 2016, issued in U.S. Appl. No. 14/481,762.
U.S. Office Action, dated May 16, 2016, issued in U.S. Appl. No. 14/216,743.
U.S. Office Action, dated May 30, 2019, issued in U.S. Appl. No. 15/376,542.
U.S. Office Action, dated Nov. 19, 2015, issued in U.S. Appl. No. 14/724,750.
U.S. Office Action, dated Nov. 25, 2014, issued in U.S. Appl. No. 14/154,019.
U.S. Office Action, dated Oct. 2, 2015, issued in U.S. Appl. No. 14/216,743.
U.S. Office Action, dated Oct. 22, 2014, issued in U.S. Appl. No. 14/290,884.
U.S. Office Action, dated Oct. 22, 2015, issued in U.S. Appl. No. 14/295,076.
U.S. Office Action, dated Oct. 26, 2016, issued in U.S. Appl. No. 15/195,911.
U.S. Office Action, dated Oct. 27, 2015, issued in U.S. Appl. No. 14/481,020.
U.S. Office Action, dated Oct. 6, 2016, issued in U.S. Appl. No. 14/640,281.
U.S. Office Action, dated Oct. 7, 2014, issued in U.S. Appl. No. 14/481,762.
U.S. Office Action, dated Oct. 7, 2014, issued in U.S. Appl. No. 14/292,844.
U.S. Office Action, dated Sep. 18, 2014, issued in U.S. Appl. No. 14/295,059.

(56) References Cited

OTHER PUBLICATIONS

U.S. Office Action, dated Sep. 29, 2014, issued in U.S. Appl. No. 14/154,009.
US Patent Trial and Appeal Board's Decision on Appeal, dated Oct. 9, 2018,issued in U.S. Appl. No. 14/216,743.
US Patent Trial and Appeal Board's Decision on Appeal, dated Oct. 9, 2018,issued in U.S. Appl. No. 14/250,256.
US Patent Trial and Appeal Board's Decision on Appeal, dated Sep. 14, 2018,issued in U.S. Appl. No. 14/481,020.
U.S. Appl. No. 61/696,525, filed Sep. 4, 2012, William Ahmed et al., entitled "Fitness Monitoring Systems and Methods Based on Continuous Collection of Physiological Data," 4700.
U.S. Appl. No. 61/736,310, filed Dec. 12, 2012, William Ahmed et al., entitled "Fitness Monitoring Systems and Methods Based on Continuous Collection of Physiological Data," 6100.
Vyas et al. (2012) "Machine Learning and Sensor Fusion for Estimating Continuous Enern:v Expenditure," *AI Maflazine*, pp. 55-61, 13pp.
Zijlstra, Wiebren, (2004) "Assessment of spatio-temporal parameters during unconstrained walking," *Eur J Appl Physiol*, 92:39-44.

\* cited by examiner

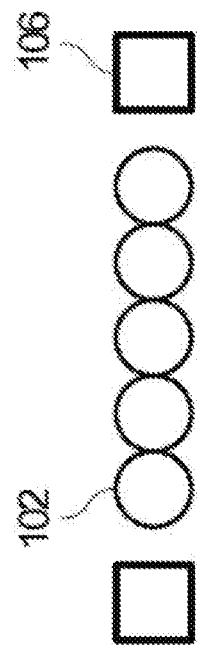
FIG. 1C
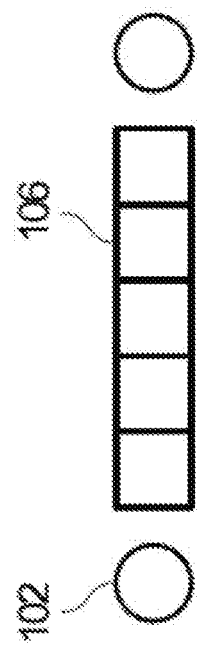
FIG. 1E
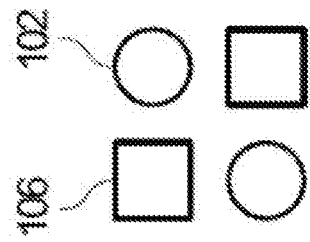
FIG. 1D
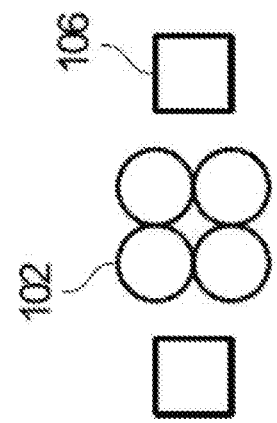
FIG. 1F
FIG. 1G

MULTIPLE SOURCE-DETECTOR PAIR PHOTOPLETHYSMOGRAPHY (PPG) SENSOR

RELATED APPLICATION

This application is a continuation of U.S. application Ser. No. 15/948,970, filed on Apr. 9, 2018, which claims the benefit of U.S. Provisional Patent Application No. 62/482,997, filed Apr. 7, 2017, titled "MULTIPLE SOURCE-DETECTOR PAIR PHOTOPLETHYSMOGRAPHY (PPG) SENSOR,". Applicant claims priority to and the benefit of each of such applications and incorporate all such applications herein by reference in its entirety.

TECHNICAL FIELD

This disclosure relates to the field of wearable devices, and particularly to techniques for using photoplethysmography (PPG) sensors to generate heart rate (HR) and other physiological metrics.

BACKGROUND

A PPG sensor may be utilized to detect the volumetric change in blood vessels. A PPG sensor usually includes a light source, typically a light-emitting diode (LED), and a light-sensitive sensor, typically a photodiode. Blood passing through the vasculature between the light source and the sensor will modulate the light path between the two, resulting in a deviation in the current produced by the photodiode. By applying various algorithms to the signal sensed by the photodiode, an HR estimate can be determined.

Further, by looking at signals corresponding to two or more wavelengths (e.g., red and infrared), a pulsatile blood oxygenation estimate (SpO2) can be obtained. SpO2 refers to a fraction of oxygen-saturated hemoglobin relative to total hemoglobin in the blood. Decreased SpO2 in the blood can lead to impaired mental function, or loss of consciousness, and may serve to indicate other serious health conditions, such as sleep apnea or cardiovascular disease. Therefore, accurately measuring SpO2 is important in certain kinds of health monitoring.

Typical PPG technologies rely on emitting wavelengths of green, red, and/or infrared (IR) light from an LED. Many wearable PPG devices use green light, as the hemoglobin absorption of light is up to 20 times greater at green wavelengths than at IR wavelengths. Additionally, in some cases, green LED light sources may provide superior results in terms of cost, form factor, and power efficiency.

SUMMARY

The systems, methods, and devices of this disclosure each have several innovative aspects, no single one of which is solely responsible for the desirable attributes disclosed herein.

One aspect of the disclosure provides a method for generating physiological metrics. The method may include obtaining one or more first PPG signals based on light received by a first light detector from a set of light sources, each light source in the set (i) having a spatial location that is different from that of another light source in the set and (ii) configured to emit light according to an emission schedule that is different from that of another light source in the set; obtaining one or more second PPG signals based on light received by a second light detector from the set of light sources; generating a physiological metric based on one or more of the first and second PPG signals; and causing the physiological metric to be displayed via a user interface on a user device.

The method of the preceding paragraph can have any sub-combination of the following features: where the set of light sources comprises at least one green light source, at least one red light source, and at least one infrared light source; where the set of light sources are provided across two or more light source packages, each light source package including at least one light source from the set and located at least 1 mm away from another one of the two or more light source packages; where the set of light sources comprises two or more light sources included in a single light source package, the two or more light sources in the light source package each configured to emit light having a wavelength that is different from another light source in the light source package; where the two or more light sources in the light source package are located within less than 1 mm from each other; where the two or more light sources comprise at least a red light source and an infrared light source; where the method further includes: obtaining a first signal of the first PPG signals based on the light received by the first light detector from a first light source in the set during a first temporal window, obtaining a second signal of the first PPG signals based on the light received by the first light detector from a second light source in the set that is different from the first light source during a second temporal window that is different from the first temporal window, and generating the physiological metric based at least in part on the first signal and the second signal; where the method further includes removing a motion component from at least one of the first and second signals based on location information associated with one or more of the first light source, the second light source, and the first light detector; where the method further includes determining a first confidence metric associated with the first signal, determining a second confidence metric associated with the second signal, and based on a determination that the first confidence metric is higher than the second confidence metric, generating the physiological metric based on the first signal; where the method further includes obtaining a first signal of the first PPG signals based on the light received by the first light detector from a first light source in the set, obtaining a second signal of the second PPG signals based on the light received by the second light detector from the first light source in the set, and generating the physiological metric based at least in part on the first signal and the second signal; where the first and second light sources are spatially located between the first and second light detectors; where the first and second light detectors are spatially located between the first and second light sources; and where the first and second light sources and the first and second light detectors are arranged such that each of the first and second light sources is equidistant from each of the first and second light detectors.

One aspect of the disclosure provides a wearable device for generating physiological metrics. The wearable device may include a plurality of light sources configured to emit light, a plurality of light detectors configured to detect the light emitted by the plurality of light sources, a display, one or more processors, and a memory. The memory may store instructions that that, when executed by the one or more processors, cause the one or more processors to: obtain one or more first PPG signals based on light received by a first light detector of the plurality of light detectors from a set of light sources of the plurality of light sources, each light source in the set (i) having a spatial location that is different from that of another light source in the set and (ii) configured to emit light according to an emission schedule that is different from that of another light source in the set; obtain one or more second PPG signals based on light received by a second light detector of the plurality of light detectors from the set of light sources; generate a physiological metric based on one or more of the first and second PPG signals; and cause the physiological metric to be displayed on the display.

The wearable device of the preceding paragraph can have any sub-combination of the following features: where the set of light sources comprises at least one green light source, at least one red light source, and at least one infrared light source; where the set of light sources are provided across two or more light source packages, each light source package including at least one light source from the set and located at least 1 mm away from another one of the two or more light source packages; where the set of light sources comprises two or more light sources included in a single light source package, the two or more light sources in the light source package each configured to emit light having a wavelength that is different from another light source in the light source package; where the two or more light sources in the light source package are located within less than 1 mm from each other; where the two or more light sources comprise at least a red light source and an infrared light source; where the instructions further cause the one or more processors to obtain a first signal of the first PPG signals based on the light received by the first light detector from a first light source in the set during a first temporal window, obtain a second signal of the first PPG signals based on the light received by the first light detector from a second light source in the set that is different from the first light source during a second temporal window that is different from the first temporal window, and generate the physiological metric based at least in part on the first signal and the second signal; where the instructions further cause the one or more processors to remove a motion component from at least one of the first and second signals based on location information associated with one or more of the first light source, the second light source, and the first light detector; where the instructions further cause the one or more processors to determine a first confidence metric associated with the first signal, determine a second confidence metric associated with the second signal, and based on a determination that the first confidence metric is higher than the second confidence metric, generate the physiological metric based on the first signal; where the instructions further cause the one or more processors to obtain a first signal of the first PPG signals based on the light received by the first light detector from a first light source in the set, obtain a second signal of the second PPG signals based on the light received by the second light detector from the first light source in the set, and generate the physiological metric based at least in part on the first signal and the second signal; where the first and second light sources are spatially located between the first and second light detectors; where the first and second light detectors are spatially located between the first and second light sources; and where the first and second light sources and the first and second light detectors are arranged such that each of the first and second light sources is equidistant from each of the first and second light detectors.

BRIEF DESCRIPTION OF THE DRAWINGS

FIGS. 1C-1I illustrate example arrangements of light sources and light detectors in accordance with aspects of this disclosure.

DETAILED DESCRIPTION

Figure 1A:
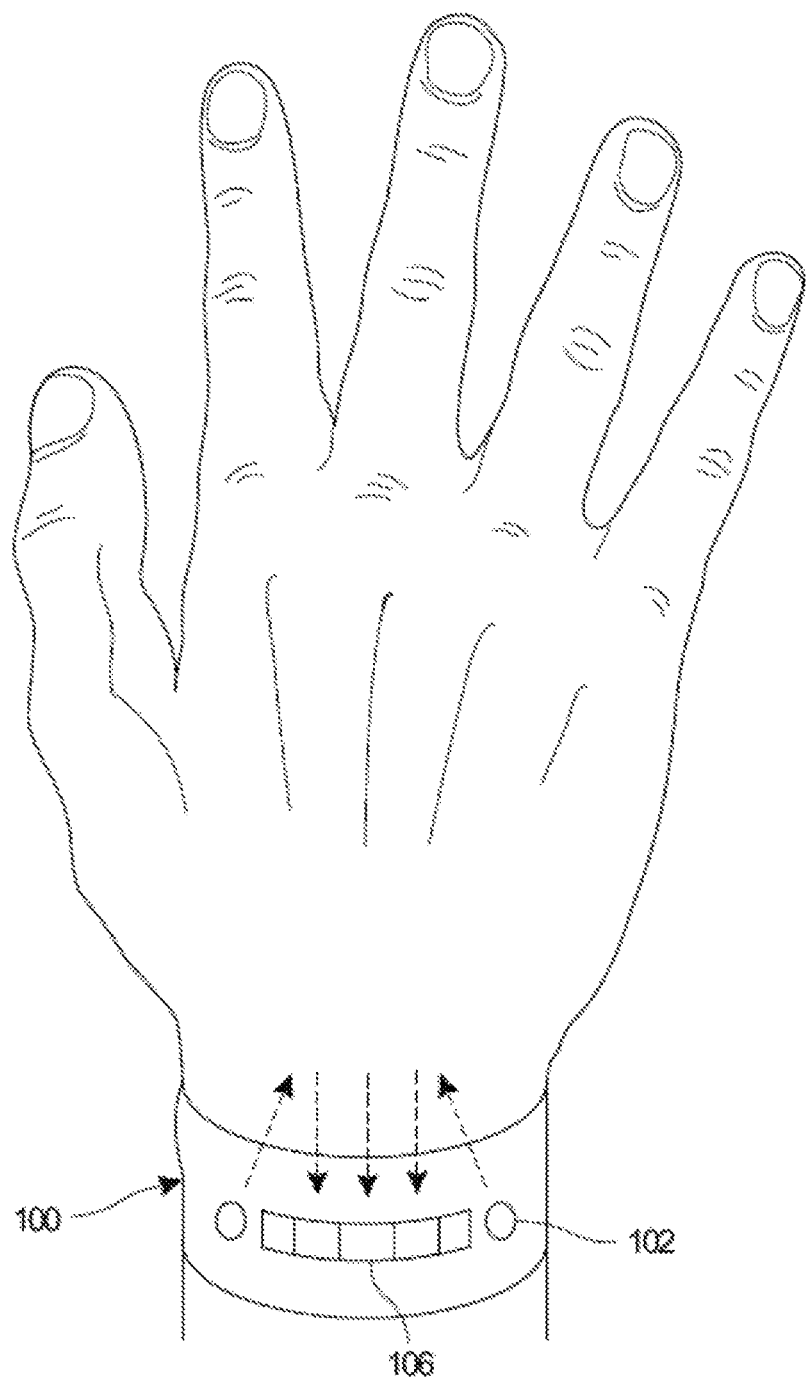
FIG. 1A illustrates an example monitoring device that may be worn by a user in accordance with aspects of this disclosure.

Existing PPG sensors can provide an effective method for measuring a user's HR. As noted above, a PPG sensor usually includes a light source, typically an LED, and a light-sensitive sensor, typically a photodiode. Using the photodiode, a PPG device including such a PPG sensor can obtain PPG signals indicative of how the blood is passing through the vessels and generate HR estimates based on the PPG signals.

Some PPG technologies rely on detecting light at a single spatial location, or adding signals taken from two or more spatial locations. Both of these approaches result in a single spatial measurement from which the HR estimate (or other physiological metrics) can be determined. In some embodiments, a PPG device employs a single light source coupled to a single detector (i.e., a single light path). Alternatively, a PPG device may employ multiple light sources coupled to a single detector or multiple detectors (i.e., two or more light paths). In other embodiments, a PPG device employs multiple detectors coupled to a single light source or multiple light sources (i.e., two or more light paths). In some cases, the light source(s) may be configured to emit one or more of green, red, and/or infrared light. For example, a PPG device may employ a single collimated light source and two or more light detectors each configured to detect a specific wavelength or wavelength range. In some cases, each detector is configured to detect a different wavelength or wavelength range from one another. In other cases, two or more detectors configured to detect the same wavelength or wavelength range. In yet another case, one or more detectors configured to detect a specific wavelength or wavelength range different from one or more other detectors). In embodiments employing multiple light paths, the PPG device may determine an average of the signals resulting from the multiple light paths before determining an HR estimate or other physiological metrics. Such a PPG device may not be able to resolve individual light paths or separately utilize the individual signals resulting from the multiple light paths.

In some cases, if the user wearing the PPG device is performing an activity involving motion (or contorting of the wrist, for example, for a wrist-worn PPG device, thereby affecting the dynamics of the blood flow within the wrist), the accuracy of the HR estimate provided by the PPG device may be reduced or compromised. The light intensity received by the light detectors may be modulated by these movements typically at an order of magnitude or greater than the desired cardiac signal. Therefore, a preprocessing step where the signal effect of these movements is removed would be desirable and improve HR estimation accuracy during motion.

In addition to the deleterious effects of motion, another cause of reduced signal quality in PPG devices may be the characteristics of the local area being sensed. For instance, signal quality can vary dramatically if a wrist-worn PPG sensor is moved only a few millimeters up or down the wrist. In addition, during motion, certain portions of the wrist-worn PPG devices may be subject to more motion depending on their location, position, and/or orientation, and PPG sensors placed on such portions may therefore result in greater degradation of the PPG signal due to motion.

Overview of Improved Techniques for Measuring HR and Other Physiological Metrics Various embodiments of the present disclosure allow a PPG device to utilize signals based on two or more independently addressable source-detector combinations such that the signal quality of the PPG device is improved, especially during activities involving motion. In some embodiments, PPG signals can be acquired via multiple light paths involving one or more sources and one or more detectors placed at different spatial locations. These multiple PPG signals are then processed to isolate the cardiac component (e.g., by removing the motion component) from the PPG signals. For example, the motion component may be removed based on inputs from the accelerometer, unsupervised learning and/or previously done supervised learning. Additionally, or alternatively, the PPG signals corresponding to these multiple light paths are compared using a quality metric such that the highest-quality PPG signal can be selected to be used for estimating HR or other physiological metrics.

To utilize two or more source-detector pairs for motion signal rejection, a PPG device can use a computer program to identify the motion component of a given signal and remove the motion component from the composite signal, leaving only the cardiac signal as a remainder. In some implementations, the temporal phase of the cardiac waveform is assumed to stay constant between different light paths, while the phase of the motion signal is expected to vary between light paths due to how the PPG sensor interacts with the skin surface during activities involving motion (e.g., pressure at the PPG/skin interface may vary depending on the spatial location of the light source and the light detector of the light path). Using this concept, PPG devices can fit mathematical models to the spatial light path signals to identify the cardiac and motion components. First, PPG signals are extracted by each source-detector combination. For example, two light sources and two light detectors would result in four source-detector combinations. A mathematical model is then fit to the different spatial points, from which characteristic signals are extracted related to the cardiac and motion components of the PPG signals. Such techniques are described in greater detail below with reference to FIG. 6. PPG devices may also implement other techniques including, but not limited to, independent component analysis (ICA) and other forms of blind source separation.

Although some embodiments are described with reference to HR or cardiac components of PPG signals, the techniques described herein may be extended to other types of physiological metrics described herein (e.g., SpO2) or other types of signals that can be extracted from the PPG signals to determine such physiological metrics. For example, in some embodiments, a method for determining an SpO2 value comprises receiving a first set of one or more PPG signals from one or more PPG sensors, which may include analog signals or digital data sampled from analog components and stored in computer memory. The first set of PPG signals may correspond to red and/or infrared light previously emitted by one or more light sources 102 after the emitted light has interacted with the user's skin, when the monitoring device is worn by the user. The first set of PPG signals may include a noise component. The method for determining the SpO2 value may further comprise receiving a second set of one or more PPG signals from the one or more PPG sensors, which may include analog signals or digital data sampled from analog components and stored in computer memory. For example, the second set of PPG signals may be obtained from different ranges of wavelengths emitted from the light source 102 than the first set of PPG signals. For example, the second set of PPG signals may be obtained from one or more green light sources 102. In some cases, the second set of PPG signals is obtained from a system within the device used for tracking a user's HR. In other cases, the second set of PPG signals is received from a system separate from HR detection. The method for determining the SpO2 value may further comprise filtering the first set of PPG signals based on a feature of the second set of PPG signals to generate a filtered set of PPG signals. Various filtering techniques may be used, depending on embodiments, to remove noise or other features from the first set of PPG signals based on a feature of the second set of PPG signals. As one example, HR may be the feature of the second set of PPG signals. In the case of HR, the device may create a filter based the detected frequency of the HR signal. Examples of filters include a low-pass filter, a high-pass filter, and a narrow band filter that excludes frequencies that are inconsistent with the frequency of the HR signal. The method for determining the SpO2 value may further comprise using one range of wavelengths to better measure an underlying signal on which the wavelengths of the first set of PPG signals operates. Based on this underlying signal (or features derived therefrom), the device can improve the first set of PPG signals based on filtering noise from the first set of PPG signals. Further, the filtered set of PPG signals can be used to create and store a SpO2 value. As an example, the filtered set of PPG signals may have a reduced or eliminated noise component and therefore may serve as a more accurate basis for creating and storing the SpO2 value.

According to some implementations, an intermediate HR estimation is performed based on PPG signals from two or more light paths. For each of the acquired PPG signals, the PPG device may determine an estimate of the HR in beats-per-minute (BPM) and compute a confidence metric associated with the PPG signal, which is indicative of the signal quality for the particular light path associated with the PPG signal. It may also be possible to compute a confidence metric without an intermediate HR estimation, for example by characterizing characteristics (e.g., statistics) of the PPG signal or filtered versions of the PPG signal. In some embodiments, each confidence metric corresponds to a single PPG signal. In other cases, each confidence metric corresponds to multiple PPG signals. For example, a confidence metric may be computed for each way of combining the PPG signals (e.g., signals A+B, signals A+C, signals B+C, signals A+B+C, etc.), as well as for various combinations of PPG signals (e.g., selecting at least two of signals A, B, and C). In other cases, one confidence metric corresponds to a single PPG signal and another confidence metric corresponds to a combination of multiple PPG signals. The PPG device can select an HR estimate from the multiple HR estimates corresponding to the multiple light paths (e.g., by selecting the HR estimate of the PPG signal having the highest confidence metric). Alternatively, the PPG device may assign different weight values to the multiple HR estimates based on the confidence metric values associated with the individual and/or multiple PPG signals and compute a final HR estimate based on the weight values. The confidence values and/or the weight values may be updated or optimized using unsupervised machine learning. The PPG device may implement hysteresis logic which prevents jumping between light paths in a short time window if the confidence metric values corresponding to the two light paths are within a threshold value. The PPG device may also implement logic configured to bias the selection of HR estimates based on user data, activity data, movement data, or other data accessible by the PPG device. The PPG device may apply a smoothing filter on the HR estimates, for example, to improve accuracy and provide a better user experience. Such techniques are described in greater detail below with reference to FIG. 7.

Advantage

One advantage in some of the embodiments described herein is that the spatial information associated with the light sources and/or light detectors can be used by different algorithms to improve HR or other physiological metric estimation accuracy of the PPG sensing device, especially when the user of the device is exercising or performing activities involving motion. Existing implementations typically rely on algorithms to improve the HR or other physiological metric estimation performance, but do not have the benefit of the extra sensor data generated based on multiple light paths.

Example PPG Device

Embodiments of the present disclosure provide PPG-based devices that utilize multiple source-detector pairs to provide more accurate HR and other physiological metrics. As shown in FIG. 1A, a PPG device 100 (also referred to herein as a monitoring device or a wearable device) worn by a user may include a plurality of light sensors 102 and a plurality of light detectors 106. As indicated by the dashed arrows, light emitted from the light sensors 102 can be reflected back to the light detectors 106. Although FIG. 1A shows an example in which the user is wearing the PPG device 100 on the inner wrist, in other embodiments, the PPG device 100 may be worn on the outer wrist or side wrist or in locations such as the ear, fingertips, ankle, neck, upper arm, torso, leg and/or forehead (e.g., such that light sources of the PPG devices are adjacent to blood vessels of a human).

Light Path

For purposes of this disclosure, the term "light path," in addition to having its ordinary meaning, refers to the probabilistic path of photons from one location to another, typically from the light source (or emitter) to the light detector (or sensor). Photons emitted by the light emitter will follow many different paths to each detector. For simplicity and clarity, the path that results from the optical power-weighted average of all the possible paths is described simply as the "light path" in some embodiments. In some alternative embodiments, "light path" refers to the path along which most of the photons travel. In yet other embodiments, "light path" refers to an approximated vector having an origin at a center of a light source and terminating anywhere in the surface area of a detector, and representing an approximate path of light from the source to the detector.

As described above, a light path represents an approximate path of light from a given source to a given detector. Thus, for example, if there are multiple sources 102 and multiple detectors 106, then a distinct light path exist between each of the multiple sources and each of the multiple detectors. Thus, consistent with the embodiments described herein, PPG signals associated with any of the aforementioned light paths may be selectively obtained and utilized for estimating HR and/or other physiological metrics. For example, the PPG signals corresponding to any of multiple paths may be compared using a quality/confidence metric such as a signal-to-noise ratio (SNR), and the PPG signal having the highest quality can be selected to be used for estimating the HR and/or other physiological metrics.

For example, FIG. 1A illustrates two light sources 102 and five light detectors 106. Each light source 102 has a light path leading to each of the light detectors 106. Thus, the example of FIG. 1A has ten unique light paths. In other embodiments, the PPG device 100 may contain any number of light sources 102 and light detectors 106. In an embodiment, light sources 102 and light detectors 106 are configured to be aligned proximate to a user's skin when PPG device 100 is worn. "Proximate" may mean any of slightly separated from, near, adjacent to, or in direct contact with, but direct contact is not required. For example, in FIG. 1A, the PPG device 100 is worn on the wrist of the user such that light sources 102 and light detectors 106 are adjacent to the dorsal side of the wrist of the user (e.g., the side of the wrist facing the same direction as the back of the hand). The positioning of the PPG device 100 as shown in FIG. 1A is provided merely as an example, and other embodiments may use alternative positioning. For example, the PPG device 100 may be positioned such that light sources 102 and light detectors 106 are proximate to the volar side of the wrist of the user (e.g., the side of the wrist facing the same direction as the palm of the hand) when the PPG device 100 is worn by the user.

PPG Device Architecture

Figure 1B:
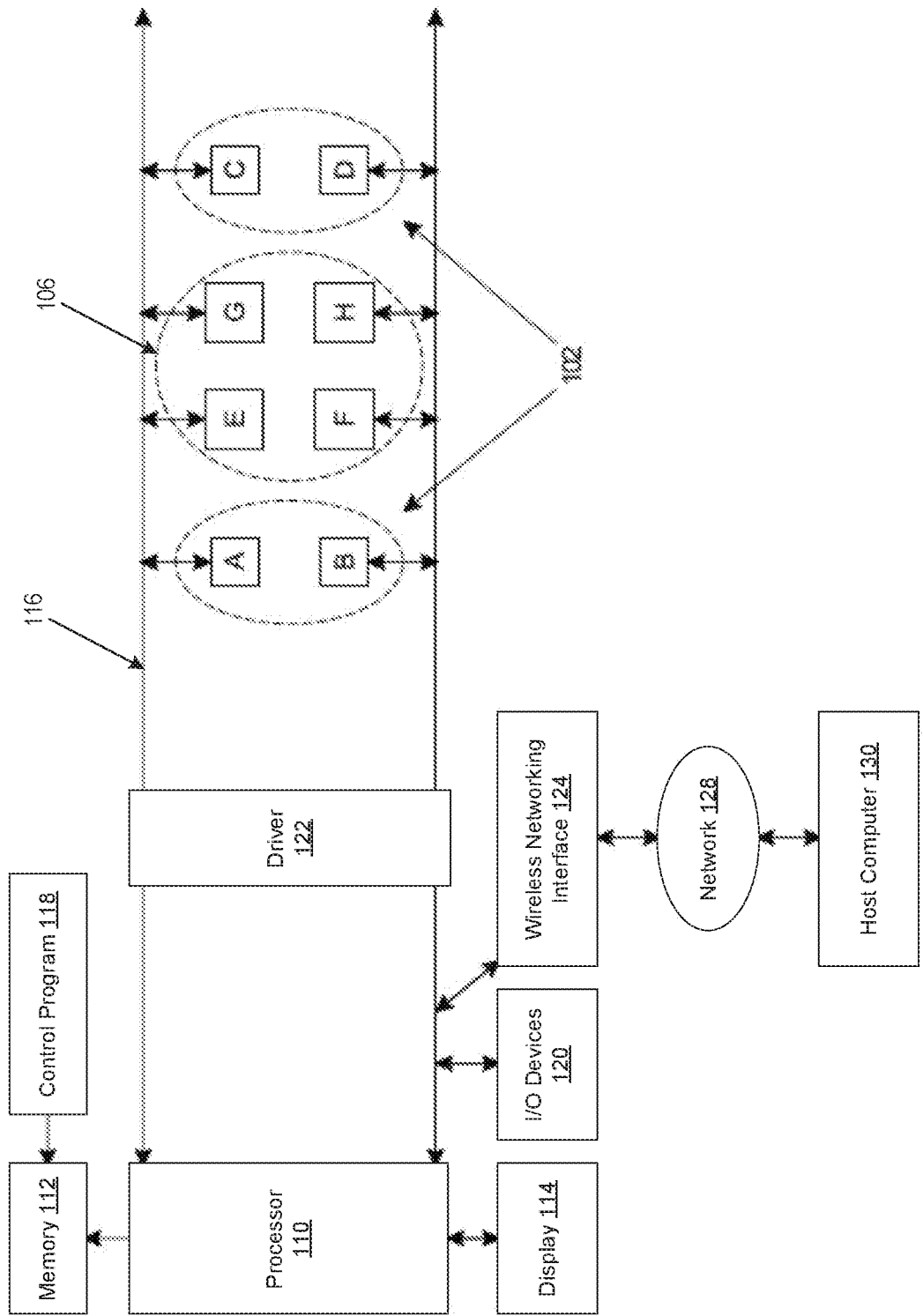
FIG. 1B illustrates an example hardware architecture of a monitoring device in accordance with aspects of this disclosure.

With reference to FIG. 1B, an example hardware architecture of the PPG device 100 is described. As shown in FIG. 1B, the PPG device 100 comprises one or more light sources 102 and one or more light detectors 106. The PPG device 100 may further comprise one or more processors 110 (also referred to herein as processor 110) coupled to memory 112, display 114, bus 116, one or more input/output (I/O) devices 120, and wireless networking interface 124. Display 114 and/or I/O devices 120 may be omitted in certain embodiments. Display 114 may comprise a liquid crystal display, light-emitting diode display, touchscreen, or other electronic digital display device. Display 114 may be programmed or configured to display data, such as HR, blood oxygen saturation ($SpO_2$) levels, and other metrics of the user. For example, the processor 110 may compute values for the physiological metrics monitored by the PPG device 100 based on one or more PPG signals generated by the light detectors 106. In an embodiment, the PPG device 100 is a wristband and the display 114 is configured such that the display faces away from the outside of a user's wrist when the user wears the PPG device. In other embodiments, the display 114 may be omitted and data detected by the PPG device 100 may be transmitted using the wireless networking interface 124 via near-field communication (NFC), Bluetooth, Wi-Fi, or other suitable wireless communication protocols to a host computer 130 for analysis, display, and/or reporting.

I/O devices 120 may include, for example, motion sensors, vibration devices, lights, loudspeakers or sound devices, microphones, or other analog or digital input or output devices. For example, in addition to the elements shown in FIG. 1B, the PPG device 100 may include one or more of biometric sensors, optical sensors, inertial sensors (e.g., accelerometer, gyroscope, etc.), barometric sensors (e.g., altimeter, etc.), geolocation sensors (e.g., GPS receiver), and/or other sensor(s).

Memory 112 may comprise RAM, ROM, FLASH memory, or other digital data storage, and may include a control program 118 comprising sequences of instructions which, when loaded from the memory and executed using the processor 110, cause the processor 110 to perform the functions that are described herein. Light sources 102 and light detectors 106 may be coupled to bus 116 directly or indirectly using driver circuitry 122 by which the processor 110 may drive the light sources 102 and obtain signals from the light detectors 106.

The host computer 130 may be coupled to the wireless networking interface 124 via one or more networks 128, which may include one or more local area networks, wide area networks, and/or internetworks using any of terrestrial or satellite links. In some embodiments, host computer 130 executes control programs and/or application programs that are configured to perform some of the functions described herein including but not limited to the processes described herein with respect to FIGS. 3-7.

In some embodiments, each light source 102 (e.g., light sources A, B, C, D) can be individually controlled, or each light detector 106 (e.g., light detectors E, F, G, H) can be individually read out when multiple detectors are used, and in such embodiments, PPG sensor data along several different light paths can be collected. For example, in the arrangement shown in FIG. 1B, if the control program 118 drives the light sources A-D one at a time, by the time the light sources A-D have each been activated once, each of the light detectors E-H would have captured four sets of data (e.g., one for each light source), resulting in 16 sets of data based on the 16 light paths. The control program 118 can utilize the collected data to provide a more accurate estimation or HR and/or other physiological metrics.

In related aspects, the processor 110 and other component(s) of the PPG device 100 may be implemented as a System-on-Chip (SoC) that may include one or more central processing unit (CPU) cores that use one or more reduced instruction set computing (RISC) instruction sets, and/or other software and hardware to support the PPG device 100.

Other Functions of PPG Device

The PPG device 100 may collect one or more types of physiological and/or environmental data from one or more sensor(s) and/or external devices and communicate or relay such information to other devices (e.g., host computer 130 or another server), thus permitting the collected data to be viewed, for example, using a web browser or network-based application. For example, while being worn by the user, the PPG device 100 may perform biometric monitoring via calculating and storing the user's step count using one or more sensor(s). The PPG device 100 may transmit data representative of the user's step count to an account on a web service (e.g., www.fitbit.com), computer, mobile phone, and/or health station where the data may be stored, processed, and/or visualized by the user. The PPG device 100 may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, $SpO_2$, blood volume, blood glucose; skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The PPG device 100 may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the PPG device 100 (and/or the host computer 130 and/or another server) may collect data from one or more sensors of the PPG device 100, and may calculate metrics derived from such data. For example, the PPG device 100 (and/or the host computer 130 and/or another server) may calculate the user's stress or relaxation levels based on a combination of HR variability, skin conduction, noise pollution, and/or sleep quality. In another example, the PPG device 100 (and/or the host computer 130 and/or another server) may determine the efficacy of a medical intervention, for example, medication, based on a combination of data relating to medication intake, sleep, and/or activity. In yet another example, the PPG device 100 (and/or the host computer 130 and/or another server) may determine the efficacy of an allergy medication based on a combination of data relating to pollen levels, medication intake, sleep and/or activity. These examples are provided for illustration only and are not intended to be limiting or exhaustive.

Source-Detector Arrangement

As discussed above, PPG devices according to the embodiments of the present disclosure includes multiple light sources and/or light detectors. FIGS. 1C-1I illustrate several example configurations of light sources 102 and light detectors 106. Other configurations of multiple sources and/or multiple detectors may be implemented, for instance by combining some of the configurations illustrated in FIGS. 1C-1I. In some cases, a light source 102 described herein may include two or more co-located light emitters that are each configured to emit light having a different center wavelength (e.g., a green light emitter, a red light emitter, and an infrared light emitter, or any combination thereof, may be packaged in a single light source 102). Such co-located light emitters may be packaged to be within less than 1 mm from each other. Alternatively or additionally, a light source 102 described herein may include a single light emitter configured to emit light having a single center wavelength (e.g., a first light source 102 may be configured to emit just green light, a second light source 102 may be configured to emit just red light, and a third light source 102 may be configured to emit just infrared light). Further, a light detector 106 described herein may be configured to detect light having a specific range of wavelengths (e.g., green light, red light, or infrared light). Alternatively or additionally, a light detector 106 described herein may be configured to detect light of multiple ranges of wavelengths (e.g., green light, red light, and infrared light, or any combination thereof).

FIG. 1C illustrates a configuration in which five light detectors are arranged in a line between two light sources 102 (e.g., in a one-dimensional layout). Light emitted by the light sources 102 are reflected towards the light detectors 106 disposed between the two light sources 102. FIG. 1D illustrates a configuration in which five light sources 102 are arranged in a line between two light detectors 106 (e.g., in a one-dimensional layout). Light emitted by the light sources 102 located between the light detectors 106 are reflected towards the light detectors 106. In some embodiments, the PPG device 100 includes two or more light detectors between the light sources. Alternatively, or additionally, the PPG device may include two or more light sources between the light detectors. The center points of all of the light sources and light detectors may be aligned along a straight line (e.g., in a one-dimensional layout).

FIG. 1E illustrates a configuration in which four light detectors 106 are arranged in a box shape (e.g., in a two-dimensional layout) between the two light sources 102. FIG. 1F illustrates a configuration in which four light sources 102 are arranged in a box shape (e.g., in a two-dimensional layout) between the two light detectors 106. Alternatively, a single detector 106 may be surrounded by multiple sources 102 (e.g., in a ring geometry), or a single source 102 may be surrounded by multiple detectors 106 (e.g., in the ring geometry). In some embodiments, the PPG device 100 includes a two-dimensional array of light detectors located between two light sources. Alternatively, or additionally, the PPG device 100 may include a two-dimensional array of light sources located between two light detectors.

FIG. 1G illustrates a configuration in which two light sources 102 and two light detectors 106 are arranged in an alternating manner in a box shape (e.g., in a two-dimensional layout). In some embodiments, the PPG device includes a two-dimensional array of light sources and light detectors, where the two-dimensional array includes the same number of light sources as the light detectors. Additionally, or alternatively, the PPG device 100 includes a two-dimensional array of light sources and light detectors, in which (i) the light sources are adjacent only to the light detectors along the horizontal direction and the vertical direction and (ii) the light detectors are adjacent only to the light sources along the horizontal direction and the vertical direction, where the horizontal direction is parallel to the surface of the user's skin and the direction in which the user's arm extends when the device is worn by the user, and the vertical direction is parallel to the surface of the user's skin and perpendicular to the direction in which the user's arm extends when the device is worn by the user. In some other embodiments, the PPG device 100 includes a two-dimensional array of light sources in light detectors, in which (i) the light sources are adjacent only to the light detectors along the horizontal direction and only to other light sources along the vertical direction and (ii) the light detectors are adjacent only to the light sources along the horizontal direction and only to other light detectors along the vertical direction, where the horizontal direction is parallel to the surface of the user's skin and the direction in which the user's arm extends when the device is worn by the user, and the vertical direction is parallel to the surface of the user's skin and perpendicular to the direction in which the user's arm extends when the device is worn by the user.

Figure 1H:
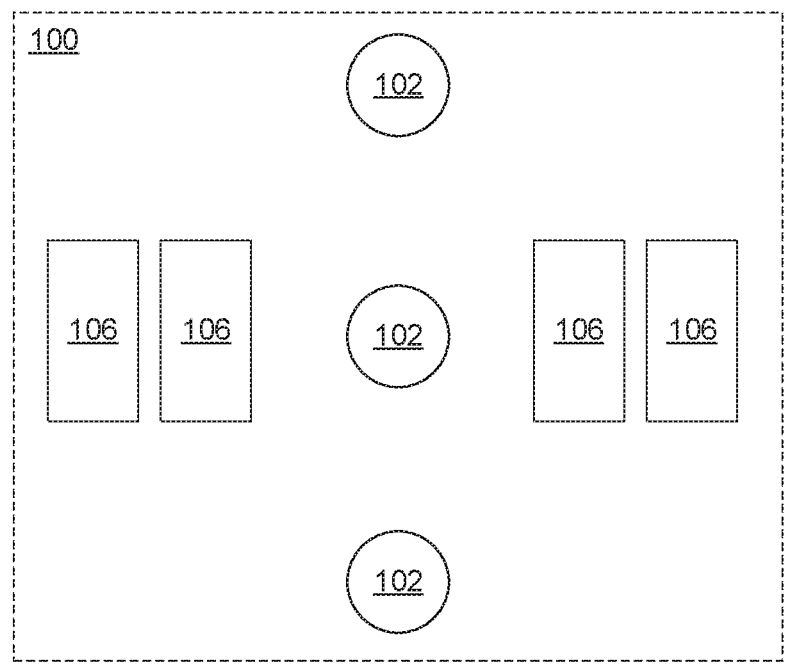

FIG. 1H illustrates a configuration in which three light sources 102 are arranged along a vertical line or axis, and in which four light detectors 106 (e.g., two inner light detectors 1061 closer to the center light source 102 and two outer light detectors 1060 that are farther away from the center light source 102) and the center light source 102 are arranged along a horizontal line or axis. In one example, the center light source 102 includes a green light emitter, a red light emitter, and an infrared light emitter, the top and bottom light sources 102 each include a green light emitter, the inner two light detectors 1061 are configured to detect green light, and the outer two light detectors 1060 are configured to detect red and infrared light. In other examples, the individual light sources 102 and light detectors 106 include other combinations of light sources or emitters.

In some embodiments, the light sources and detectors are arranged such that the distance between a green light source and a green light detector is shorter than the distance between a red or infrared light source and a red or infrared light detector. For example, as shown in FIG. 1H, the distance between the center light source 102 and the inner light detectors 1061 may be shorter than the distance between the center light source 102 and the outer light detectors 1060. In other embodiments, the light sources and detectors are arranged such that the distance between a green light source and a green light detector is greater or equal to the distance between a red or infrared light source and a red or infrared light detector.

Figure 1I:
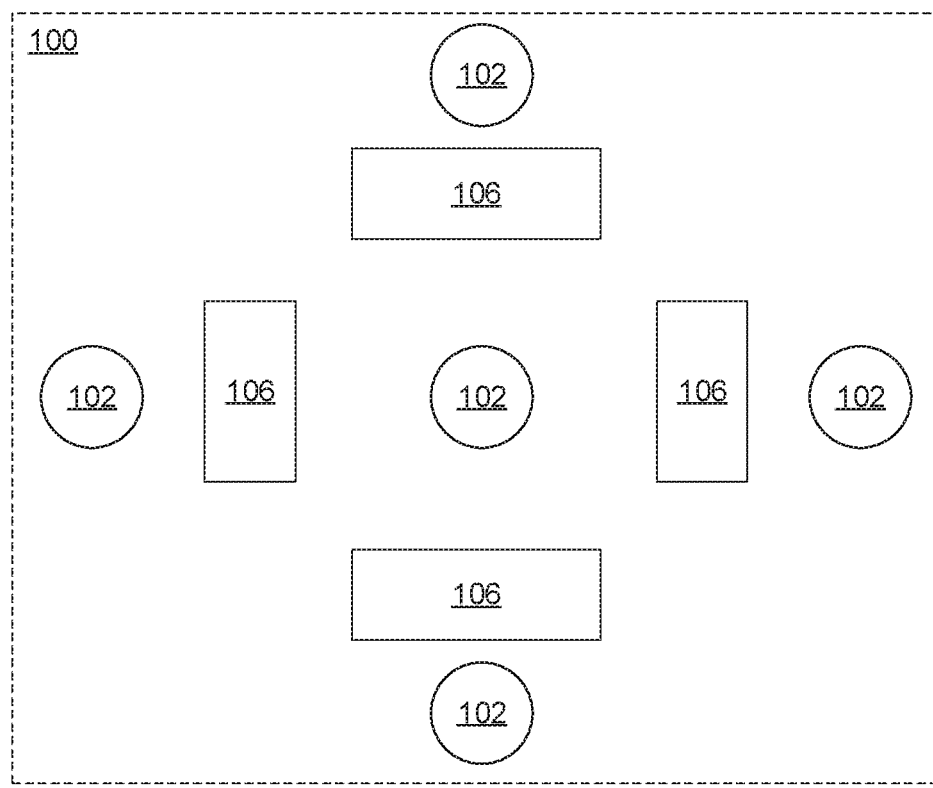

FIG. 1I illustrates a configuration in which five light sources 102 and four light detectors 106 are arranged in the shape of a cross, each leg of the cross having a light detector 106 and a light source 102, in that order, along a radial direction from the center of the cross, and a light source 102 being positioned at the center of the cross. In one example, the center light source 102 includes a green light emitter, a red light emitter, and an infrared light emitter, the left and right light sources 102 each include a red light emitter and an infrared light emitter, the top and bottom light sources 102 each include a green light emitter, the left and right light detectors 106 are configured to detect green light, and the top and bottom light detectors 106 are configured to detect red and infrared light. In other examples, the individual light sources 102 and light detectors 106 include other combinations of light sources or emitters. In the example of FIG. 1I, light emitted by the top, center, and/or bottom light sources 102 and received by the top and/or bottom light detectors 106 would be along one rotational axis (e.g., first rotational axis) of the device, and light emitted by the left, center, and/or right light sources 102 and received by the left and/or right light detectors 106 would be along another rotational axis of the device (e.g., second rotational axis, which, in this example, is orthogonal to the first rotational axis). In other implementations, additionally or alternatively, two or more axes that are not orthogonal to each other may be utilized (e.g., at an angle other than 90 degrees).

Although not shown in FIGS. 1C-1I, the PPG device 100 may include other arrangements. For example, the PPG device 110 may include a single green light source and multiple light detectors (e.g., two, three, or more light detectors). As another example, the PPG device 110 may include a red light source, a single infrared light source, and two red and infrared light detectors. In some cases, one or more of the elements shown in FIGS. 1C-1I may be omitted. Further, in some implementations, one or more of the arrangements of FIGS. 1C-1I may be flipped (horizontally or vertically) or rotated by a specific degree value (e.g., 30 degrees, 45, degrees, 60 degrees, 90, degrees, 180 degrees, etc, along either a clockwise direction or a counterclockwise direction).

Perspective View of Example Wearable Device

Figure 2:
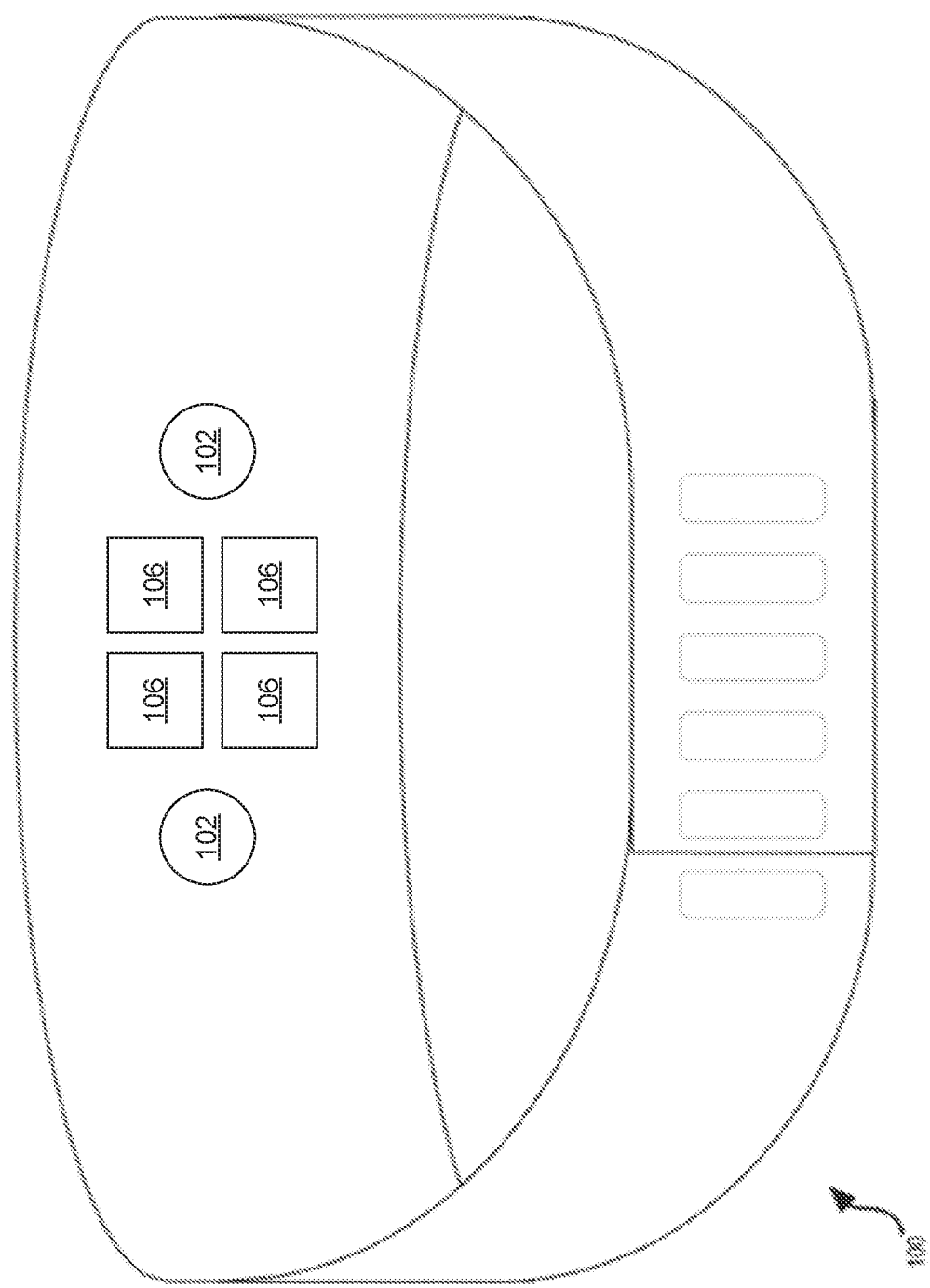
FIG. 2 illustrates a perspective view of a monitoring device in accordance with aspects of this disclosure.

FIG. 2 illustrates a schematic perspective view of a PPG device in one embodiment. In the example of FIG. 2, the PPG device 100 includes an arrangement of light sources 102 and light detectors 106 similar to that shown in FIG. 1E. In this embodiment, the PPG device 100 comprises a wrist band in which the light sources 102 and light detectors 106 are mounted on or within an underside of the PPG device 100 such that the light sources 102 and light detectors 106 face the user's skin when worn on the user's wrist. The PPG device 100 may include a fastening means to attach the device to a portion of a user's body. The fastening means may be a strap that is passed through a receiving portion of the strap and fastened with hook and/or loop fasteners. Other fastening means may include clips, latches, hook-and-loop fasteners such as VELCRO®, clasps, ties, and/or adhesives. The fastening means may be located on any side of the PPG device 100 such that the fastening device does not interfere with movement or activity.

In an embodiment, the PPG device 100 may comprise a processor, memory, user interface, wireless transceiver, one or more environmental sensors, and one or more biometric sensors other than the detector 106. For example, embodiments may be implemented using a monitoring device of the type shown in U.S. Pat. No. 8,948,832 of Fitbit, Inc., San Francisco, Calif., the entire contents of which are hereby incorporated by reference for all purposes as if fully set forth herein. In other words, the monitoring device of the type shown in U.S. Pat. No. 8,948,832 could be modified based upon the additional disclosure herein to result in a working activity monitoring apparatus capable of performing the functions that are described herein. Therefore, the present disclosure presumes that the reader knows and understands U.S. Pat. No. 8,948,832, and this disclosure is directed to persons having a level of skill sufficient to modify or adapt the monitoring device of the type shown in U.S. Pat. No. 8,948,832 based upon the additional disclosure herein to result in a working PPG device capable of performing the functions that are described herein.

Light Sources

In various embodiments, the light sources 102 comprise electronic semiconductor light sources, such as LEDs, or produce light using any of filaments, phosphors, or laser. In some implementations, each of the light sources 102 emits light having the same center wavelength or within the same wavelength range. In other cases, at least one light source 102 may emit light having a center wavelength that is different from another one of the light sources 102. The center wavelengths of the light emitted by the light sources 102 may be in the range of 495 nm to 570 nm. For example, a particular green light source 102 may emit light with a center wavelength of 528 nm. In other embodiments, one or more of the light sources 102 may emit red light (e.g., 660 nm center wavelength) or IR light (e.g., 940 nm center wavelength). In some embodiments, one or more of the light sources 102 may emit light with peak wavelengths typically in the range of 650 nm to 940 nm. For example, in various embodiments, a particular red light source may emit light with a peak wavelength of 660 nm, and an infrared light source may emit light with peak wavelengths in the range of 750 nm to 1700 nm. By way of example and not limitation, a particular infrared light source may emit light with a peak wavelength of 730 nm, 760 nm, 850 nm, 870 nm, or 940 nm. In some cases, commercial light sources such as LEDs may provide output at about 20 nm intervals with a center wavelength tolerance of +/−10 nm from the manufacturer's specified wavelength and thus one possible range of useful peak wavelengths for the light sources is 650 nm to 950 nm. The green light sources may be configured to emit light with wavelengths in the range of 495 nm to 570 nm. For example, a particular green light source may emit light with a wavelength of 528 nm. The green light sources may be equally spaced from light detectors 106 as the pairs of red and infrared light sources. For example, if the distance between light detectors 106 and a center of a first red light source is 2 mm, the distance between light detectors 106 and a green light source may also be 2 mm (e.g., equidistant). In some other cases, the distance between the light detectors and one or more light sources is not equidistant. Further, in some embodiments, one or more of the light sources 102 may comprise a single LED package that emits multiple wavelengths, such as green, red and infrared wavelengths, at the same or substantially the same (e.g., less than 1 mm difference) location with respect to multiple detectors. Such LEDs may include multiple semiconductor elements co-located using a single die in a single package.

The spacing of the light sources 102 may be measured from the side of the light source or the center of the light source. For example, the light sources may be configured such that the center of each light source is at a first distance from the edge of the closest one of the light detectors 106. In some embodiments, the first distance may be 2 mm. In some implementations, each light source is located at a second distance from the closest one of the light sources 102, and each light detector is located at a third distance from the closest one of the light detectors 106. In some embodiments, the second and third distances are identical to the first distance. In other embodiments, each of the second and third distances is different from the first distance. The second distance may be identical to or different from the third distance. The particular magnitude of the spacing may depend on a number of factors and this disclosure does not limit the embodiments to any particular spacing. For example, spacing in a range of 1 mm (or less) to 10 mm would be workable in various embodiments.

In some embodiments, independent control of all light sources is provided. In other embodiments, several light sources are controlled together as a gang or bank. A benefit of independent control of each light source, or independent readout from each of multiple detectors (e.g., obtaining independent signals based on the same or different light wavelengths from each of multiple detectors), is that a multiple light path approach may be used to improve the estimation of HR and/or other physiological metrics, as discussed further herein.

Light Detectors

Light detectors 106 comprise one or more sensors that is/are adapted to detect wavelengths of light emitted from light sources 102. A particular light source 102 combined with a particular detector 106 may comprise a sensor such as a PPG sensor. A first PPG sensor and a second PPG sensor can share components, such as the same light sources and/or detectors, or have different components and thus the term "PPG sensor," in addition to having its ordinary meaning, may refer to any of such arrangements although actual embodiments may use multiple components in implementing a PPG sensor. The term "PPG device," in addition to having its ordinary meaning, may refer to a device including a PPG sensor. A light detector 106, in an embodiment, may comprise one or more detectors for detecting each different wavelength of light that is used by the light sources. For example, a first detector may be configured to detect light with a wavelength of 560 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths. The light detectors 106 may comprise any of a photodiode, phototransistor, charge-coupled device (CCD), thermopile detector, or complementary metal-oxide-semiconductor (CMOS) sensor. The light detectors 106 may comprise multiple detector elements, as further described herein. One or more of the detectors may comprise a bandpass filter circuit.

In other embodiments, detector 106 comprises one or more detectors configured to detect multiple wavelengths of light. For example, a single detector may be configured to tune to different frequencies based on data received from an electrical digital microprocessor coupled to detectors 106. In another way, the single detector may include multiple active areas where each active area is sensitive to a given range of wavelengths. In an embodiment, a single detector is configured to detect light with wavelengths in the red and IR frequencies and a second detector is configured to detect light with wavelengths in the green frequencies. Further, each of the light sources 102 may use any of one or more different wavelengths of light as previously described.

In an embodiment, light detectors 106 are mounted in a housing with one or more filters that are configured to filter out wavelengths of light other than wavelengths emitted by light sources 102. For example, a portion of the housing may be covered with a filter which removes ambient light other than light in wavelengths emitted by light sources 102. For example, signals from light sources 102 may be received at the light detectors 106 through an ambient light filter that filters out an ambient light source that generates an ambient light with a wavelength that is different from the wavelength that is detected by the detector. Although LEDs and photodiodes are used as examples of the light sources 102 and the light detectors 106, respectively, the techniques described herein may be extended to other types of light sources. For example, the PPG device 100 may include (i) single or multiple LEDs and a multi-element photodetector (e.g., a camera sensor), (ii) an LED array and single or multiple photodiodes, (iii) spatial light modulator (SLM) (e.g., a digital micromirror device [DMD] or a liquid crystal on silicon [LCoS] device) and single or multiple LEDs, other combinations thereof, or other configurations of light sources and detectors.

Example Techniques for Generating Heart Rate and Other Physiological Metrics

Certain flow diagrams are presented herein to illustrate various methods that may be performed by example embodiments. The flow diagrams illustrate example algorithms that may be programmed, using any suitable programming environment or language, to create machine code capable of execution by a CPU or microcontroller of the PPG device 100. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, OBJECTIVE-C, C++, JAVA, or other human-readable languages and then compiled, assembled, or otherwise transformed into machine code that can be loaded into ROM, EPROM, or other recordable memory of the activity monitoring apparatus that is coupled to the CPU or microcontroller and then executed by the CPU or microcontroller.

In an embodiment, PPG signals obtained from multiple light paths may be processed to filter or reject signal components that are associated with motion of the user, using a computer program to identify the motion component of the signal and remove the identified motion component from the composite signal, leaving the cardiac component as a remainder or final signal.

In various embodiments, the methods of FIGS. 3-7 may be performed by one or more of: firmware operating on the PPG device or a secondary device, such as a mobile device paired to the PPG device, a server, host computer 130, and the like. For example, the PPG device may execute operations relating to generating the PPG signals which are uploaded or otherwise communicated to a server that performs operations for removing the motion components and creating a final estimate value for HR, SpO2, and/or other physiological metrics. Alternatively, the PPG device may execute operations relating to generating the PPG signals and removing the motion components to produce a final estimate value for HR, SpO2, and/or other physiological metrics local to the PPG device 100. In this case, the final estimate may be uploaded or otherwise communicated to a server such as host computer 130 that performs other operations using the value.

Figure 3:
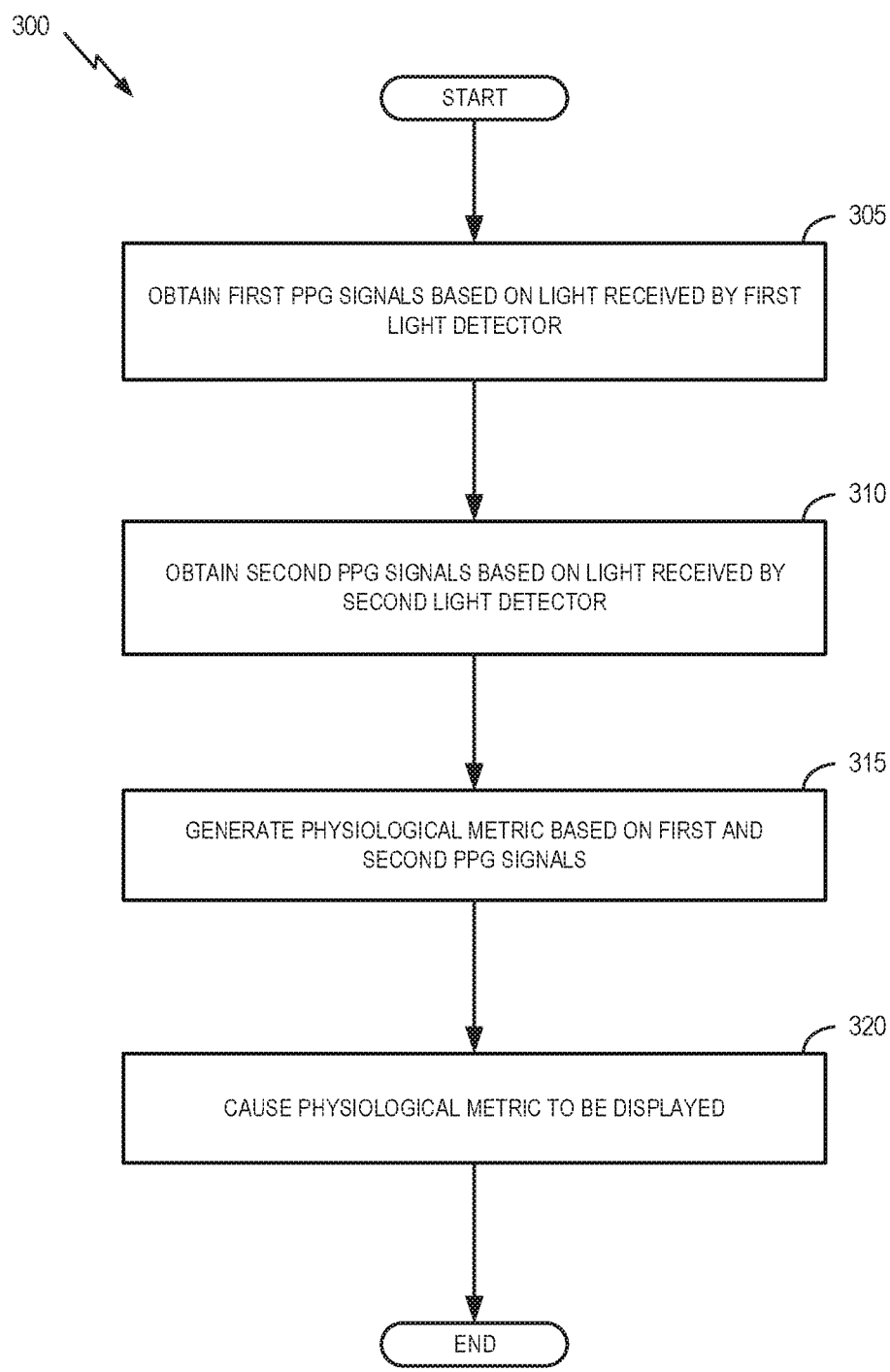
FIG. 3 illustrates an example method of generating a physiological metric using multiple light paths in accordance with aspects of this disclosure.

Generating Estimate for Physiological Metric based on Multiple Source-Detector Pairs FIG. 3 illustrates an example method of generating a physiological metric using multiple light paths in accordance with aspects of this disclosure. The method 300 may be operable by a PPG device 100, or component(s) thereof, for generating HR or other physiological metrics in accordance with aspects of this disclosure. For example, the steps of method 300 illustrated in FIG. 3 may be performed by a processor 110 of the PPG device 100. In another example, a user device (e.g., mobile phone) or a server in communication with the PPG device 100 may perform at least some of the steps of the method 300. For convenience, the method 300 is described as being performed by the processor 110 of the PPG device 100.

At block 305, the processor 110 obtains one or more first PPG signals based on light received by a first light detector from a set of light sources. Each light source in the set may have a spatial location that is different from that of another light source in the set with respect to the first light detector. Further, each light source in the set may be configured to emit light according to an emission schedule that is different from that of another light source in the set. For example, a first light source in the set may emit light for a given time period at even seconds (e.g., 2, 4, 6, etc. 2/4, 4/4, 6/4, etc., or 2/8, 4/8, 6/8, etc., to name a few examples), and a second light source in the set may emit light for a given time period at odd seconds (e.g., 1, 3, 5, etc. 1/4, 3/4, 5/4, etc., or 1/8, 3/8, 5/8, etc., to name a few examples). The first PPG signals may be obtained from the one or more light detectors 106 based upon light sources operating at any of the frequencies that have been described above. For example, by executing instructions stored in memory 112 of FIG. 1B as control program 118, the processor 110 may signal the driver 122 to activate one, some, or all of the light sources 102, which produce light directed toward blood vessels, which is then reflected to the first light detector. The first light detector produces a responsive signal to the bus 116 that is sent to the processor 110 and then stored in a register of the processor 110 or in the memory 112. The first PPG signals may be represented in any suitable form capable of being processed by a processor, such as the analog signals or digital data sampled from the analog components and stored in computer memory. In an example, the first PPG signals may correspond to green light previously emitted by a light source (or light sources) after the emitted light has interacted with a user's skin, when the PPG device 100 is worn. The first PPG signals may include a motion component and a cardiac component. In another example, the first PPG signals may include a motion component and another physiological component.

At block 310, the processor 110 obtains one or more second PPG signals based on light received by a second light detector from the set of light sources, each light source in the set having a spatial location that is different from another light source in the set with respect to the second light detector. For example, in a manner similar to that described above for block 302, the processor 110 drives the set of light sources 102 and obtains second PPG signals from the second light detector different from the first light detector discussed at block 305. Again, the second set of PPG signals may be represented in any suitable form capable of being processed by a processor, such as the analog signals or digital data sampled from the analog components and stored in computer memory. In an example, the second PPG signals may correspond to green light previously emitted by a light source (or light sources) after the emitted light has interacted with a user's skin, when the PPG device 100 is worn. The second PPG signals may include a motion component and a cardiac component. In another example, the first PPG signals may include a motion component and another physiological component. In some embodiments, the light sources that are used to obtain the first and second PPG signals may use light having the same wavelength.

At block 315, the processor 110 generates a physiological metric based on one or more of the first and second PPG signals. Various techniques for generating the HR, SpO2, and/or other physiological metric value may be used. For example, template matching based on a template previously created and stored from a high-quality PPG signal can be used to provide filter coefficients for a matched filter to maximize the signal-to-noise ratio, or an adaptive filter may be used that tunes a band-pass in real-time based upon heartbeat data derived from the PPG datasets, usually based upon green light sources. Once an HR estimate or other metrics has/have been generated, signals, data values, or data points that are available or apparent in the second PPG signals may be used to modify or improve the first PPG signals so that the resulting modified or improved first PPG signals can be transformed into a more accurate HR estimate. For example, if the intensity of the motion artifact signal varies in space between two or more light paths (i.e. source-detector pairs), a mathematical model can be applied to this spatial intensity difference to remove the motion artifact signal, thus isolating the signal of interest (e.g. cardiac or HR signal).

At block 320, the processor 110 causes the physiological metric to be displayed via a user interface on a user device. For example, the processor 110 may drive the display 114 to display the generated HR, SpO2, and/or other physiological metric value. In other embodiments, the method 300 may be programmed to cause uploading the estimated HR, SpO2, and/or other physiological metric value to host computer 130 for further processing, display, or reporting.

In the method 300, one or more of the blocks shown in FIG. 3 may be removed (e.g., not performed) and/or the order in which the method 300 is performed may be switched. For example, in some embodiments, block 320 may be omitted. In some embodiments, additional blocks may be added to the method 300. The embodiments of the present disclosure are not limited to or by the example shown in FIG. 3, and other variations may be implemented without departing from the spirit of this disclosure.

Time Multiplexing

In some embodiments, a single light detector 106 receives reflected light originating from multiple light sources 102. The light detector 106 may distinguish one PPG signal based on light emitted by light source A from another PPG signal based on light emitted by light source B by using time multiplexing (e.g., at block 305 to distinguish among the first PPG signals, and at block 310 to distinguish among the second PPG signals). In some embodiments, light source A emits light according to a first emission schedule that is different from a second emission schedule of light source B. The first emission schedule may specify that light source A is to emit light for X seconds every Y seconds, and the second emission schedule may specify that light source B is to emit light for P seconds every Q seconds. In some cases, X may equal A, and Y may equal B. In other cases, each of X, Y, P, and Q may have the same value. In some cases, the period during which light source A emits light may differ from the period during which light source B emits light by an offset. For example, the PPG device 100 may activate (e.g., emit light via) light source A during a temporal window T1 (without emitting any light via light source B during T1) and activate light source B during a temporal window T2 (without emitting any light via light source A during T2). The light emitted by the light source A during T1 may be detected by the light detector during a temporal window T1' and the light emitted by the light source B during T2 may be detected by the light detector during a temporal window T2'. Thus, the PPG device 100 can determine first PPG signals originating from light source A based on light detected during T1' and determine second PPG signals originating from light source B based on light detected during T2'. In some embodiments, there is no temporal gap between T1 and T2 (and/or T1' and T2'). In other embodiments, there is a temporal gap between T1 and T2 (and/or T1' and T2'). In some embodiments, there is a partial overlap between T1 and T2.

In some embodiments, at most one light source is emitting light at any given moment. In some embodiments, as long as any light source is emitting light, all of the light detectors are sensing reflected light from the activated light source(s). In some implementations, an internal clock is maintained, and the processor 110 may identify the specific light path (e.g., the light source and the light detector) based on the internal clock and a light source activation schedule indicative of which light sources are emitting during which temporal windows.

In some implementations, a single amplifier is used to amplify the signals generated by multiple light detectors 106, and the use of the multiple light detectors 106 may also be time-multiplexed. For example, the amplifier may amplify signals from light detector A during T0-T1, amplify signals from light detector B during T1-T2 (or T2-T3 with the amplifier not amplifying any signals during T1-T2), and so on. In other cases, each light detector 106 may be associated with a separate amplifier and multiple amplifiers may amplify signals generated by multiple light detectors 106 during a given time period. Although time multiplexing is described herein as a method of distinguishing between different PPG signals, other multiplexing techniques such as frequency multiplexing and wavelength multiplexing may be used to distinguish the PPG signals.

Spatially Resolving Measurements

The PPG device 100 may utilize the spatial location associated with each of the light sources 102 and the light detector 106 to further improve the estimate for HR, SpO2, and/or other physiological metric. In some embodiments, the PPG device 100 compares the PPG signals determined based on two (or more) unique light paths and identifies any discrepancy among the PPG signals. For example, if the phases of the two PPG signals are different, the PPG device 100 may discard one of the signals (e.g., based on the signal quality). In some cases, the PPG device 100 may determine the cause of the discrepancy and take different actions based on the cause. For example, if the PPG signals indicate that the discrepancy may be caused by the movement of the PPG device 100, the PPG device 100 may average two or more of the PPG signals and generate the estimate for HR, SpO2, and/or other physiological metric based on the averaged signal(s). On the other hand, if the PPG signals indicate that the discrepancy may be caused by the placement of the sensors or a foreign object in the light path (e.g., hair or other objects), the PPG device 100 may discard the affected PPG signals and generate the estimate for HR, SpO2, and/or other physiological metric based on the remaining PPG signal(s). For example, if the PPG device 100 determines that light paths involving light sources located on one side of the PPG device 100 are underperforming, the PPG device 100 may generate the estimate for HR, SpO2, and/or other physiological metric based on light paths involving light sources on the opposite side of the PPG device 100.

In some embodiments, the estimation for HR, SpO2, and/or other physiological metric may be agnostic to the spatial arrangement of the light sensors and detectors. For example, the PPG device 100 may calculate a spatially-agnostic metric for each PPG signal and generate the estimate for HR, SpO2, and/or other physiological metric based on the PPG signal having the most desirable metric value.

Figure 4:
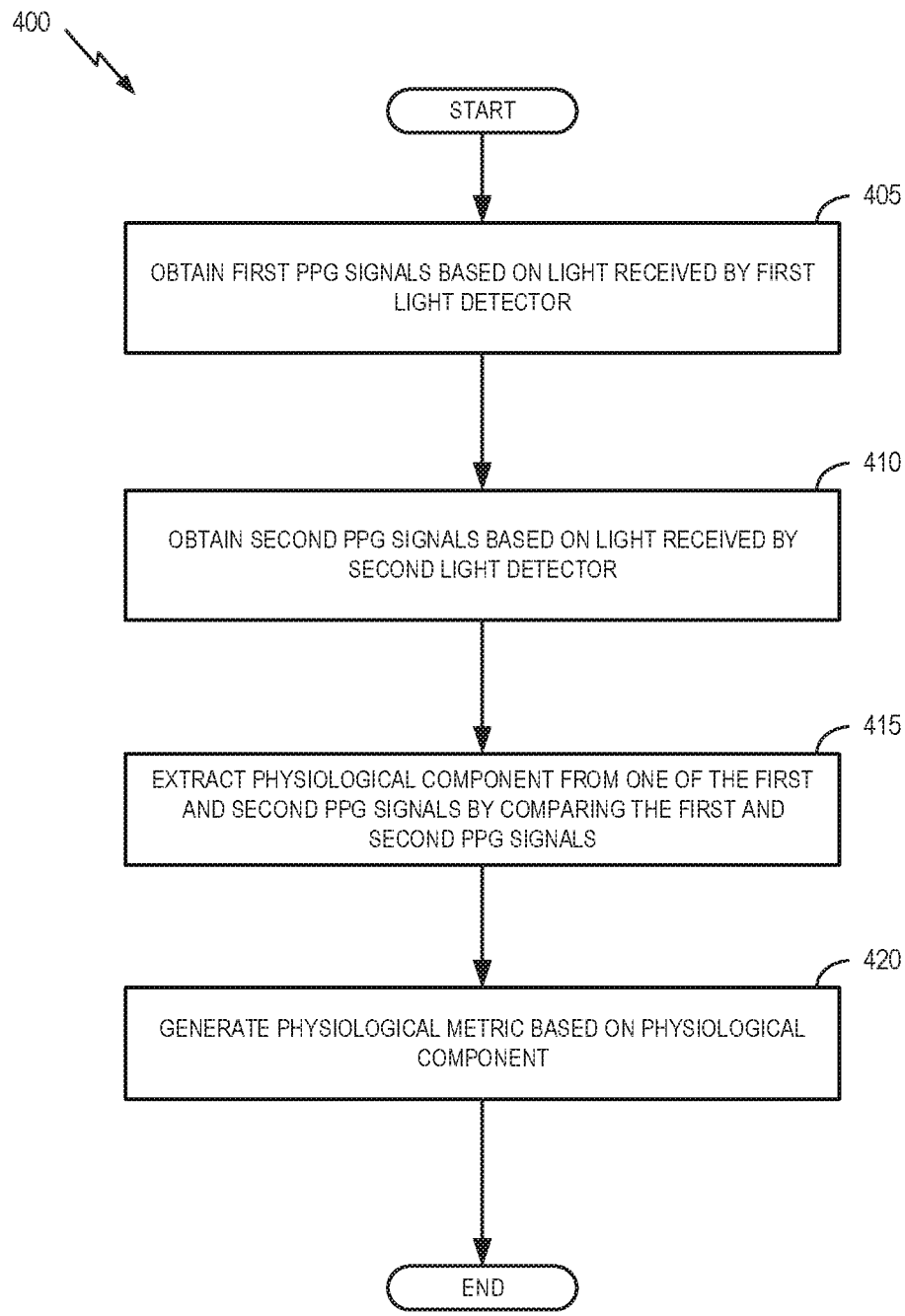
FIG. 4 illustrates another example method of generating a physiological metric using multiple light paths in accordance with aspects of this disclosure.

Generating Estimate for Physiological Metric based on Multiple Source-Detector Pairs FIG. 4 illustrates an example method of generating a physiological metric using multiple light paths in accordance with aspects of this disclosure. The method 400 may be operable by a PPG device 100, or component(s) thereof, for generating HR or other physiological metrics in accordance with aspects of this disclosure. For example, the steps of method 400 illustrated in FIG. 4 may be performed by a processor 110 of the PPG device 100. In another example, a user device (e.g., mobile phone) or a server in communication with the PPG device 100 may perform at least some of the steps of the method 400. For convenience, the method 400 is described as being performed by the processor 110 of the PPG device 100.

At block 405, the processor 110 obtains one or more first PPG signals based on light received by a first light detector from a set of light sources, each light source in the set having a spatial location that is different from another light source in the set with respect to the first light detector. The processor 110 may obtain the first PPG signals in a manner similar to that described with reference to block 305.

At block 410, the processor 110 obtains one or more second PPG signals based on light received by a second light detector from the set of light sources, each light source in the set having a spatial location that is different from another light source in the set with respect to the second light detector. The processor 110 may obtain the second PPG signals in a manner similar to that described with reference to block 310.

At block 415, the processor 110 extracts a physiological component from at least one of the first and second PPG signals by comparing the first and second PPG signals. For example, the physiological component may be a cardiac component. In another example, the physiological component may be a component other than a cardiac component and usable to generate a physiological metric. As discussed herein, the processor 110 may compare the first and second PPG signals to identify the motion component. For example, light paths involving light sources having different spatial locations may have different motion characteristics. For example, signals from a first light path may be known to be more sensitive to blood flow (or a factor other than motion) or otherwise have a relatively higher cardiac component (or another physiological component) in comparison to a motion component, while signals from a second light path may be more sensitive to motion or otherwise have a relatively higher motion component in comparison to a cardiac component (or another physiological component). With such data, the method may use the first light path to sense the cardiac component (or another physiological component) of a signal and the second, different light path to sense the motion component. As a non-limiting example, the second light path may be one where the light detector is further away from the light source in comparison to the first light path.

In some embodiments, if the processor 110 determines that the majority of a PPG signal (e.g., one of the first and second PPG signals) is a cardiac component (or another physiological component), the processor 110 may determine the estimate for HR, SpO2, and/or other physiological metric based on the PPG signal. If the processor 110 determines that the majority of a PPG signal (e.g., one of the first and second PPG signals) is a motion component, the processor 110 may subtract the motion component from the signal (e.g., motion component determined based on accelerometer readings) (or otherwise modify the PPG signal to reduce the effect of the motion component) and determine the estimate for HR, SpO2, and/or other physiological metric based on the PPG signal without the motion component. In some embodiments, for the purpose of determining an HR or a cardiac component, any PPG signal outside the range of a cardiac signal may be discarded. For example, if the PPG device 100 determines that a PPG signal would yield an HR (or BPM) estimate of 300, the PPG device 100 may discard the PPG signal. In some implementations, if the PPG device 100 that the PPG device 100 is undergoing a periodic motion (e.g., based on activity detection or based on sensor data), the PPG device 100 may identify the motion component corresponding to the periodic motion and remove the motion component from the PPG signals. Techniques for motion component removal (e.g., motion artifact removal) are discussed in U.S. Pat. No. 9,005,129 of Fitbit, Inc., San Francisco, Calif., the entire contents of which are hereby incorporated by reference for all purposes as if fully set forth herein. Other techniques that can be used include, but are not limited to, ICA and other forms of blind source separation.

At block 420, the processor 110 generates a physiological metric based on the physiological component. For example, the processor 110 may drive the display 114 to display the generated value for HR, SpO2, and/or other physiological metric. In other embodiments, the method 400 may be programmed to cause uploading the estimated value for HR, SpO2, and/or other physiological metric to host computer 130 for further processing, display, or reporting.

In the method 400, one or more of the blocks shown in FIG. 4 may be removed (e.g., not performed) and/or the order in which the method is performed may be switched. In some embodiments, additional blocks may be added to the method 400. The embodiments of the present disclosure are not limited to or by the example shown in FIG. 4, and other variations may be implemented without departing from the spirit of this disclosure.

Measuring Heart Rate based on PPG and Motion Data

Figure 5:
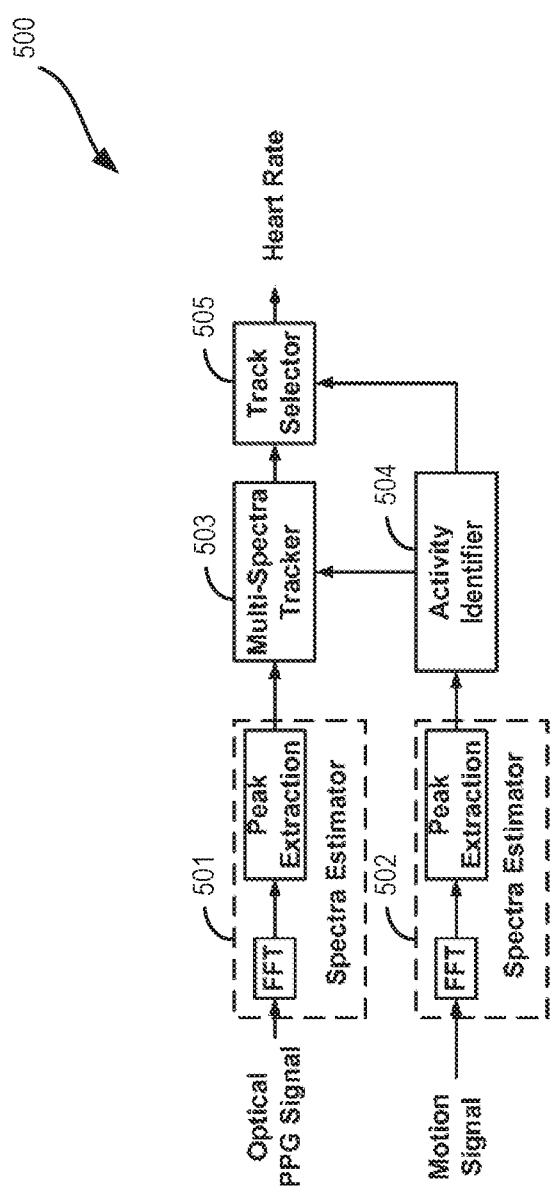
FIG. 5 is an example block diagram of a system used for determining HR estimate in accordance with aspects of this disclosure.

FIG. 5 is an example block diagram of a system used for determining HR in accordance with aspects of this disclosure. As shown in FIG. 5, the PPG device 100 may include a system 500 of circuit components for determining the HR of the user based on an optical PPG signal (e.g., received by one or more light detectors 106 of the PPG device 100) and a motion signature (e.g., received from an accelerometer in the PPG device 100). As used herein, a motion signature may refer to any biometric signature or signal that may be received from and/or based on output data from one or more of sensors, such as, for example, inertial sensor(s) (e.g., accelerometer(s) and gyroscope(s)), barometric sensors(s) (e.g., altimeter(s)), which may be indicative of the activity and/or physiological state of a user of the PPG device 100. The system 500 may be implemented by hardware components and/or in software executed by the processor 110. The system 500 may include first and second spectra estimators 501 and 502, a multi-spectra tracker 503, an activity identifier or discriminator 504, and a track selector 505. Each of the first and second spectra estimators 501 and 502 may include a Fast Fourier Transform (FFT) block and a peak extraction block. In the example of FIG. 5, the activity identifier 504 may use the peaks extracted from the motion signature to determine the activity that the user is performing (e.g., sedentary, walking, running, sleeping, lying down, sitting, biking, typing, elliptical, weight training, swimming, etc.). This determination of the current activity of the user may be used by the multi-spectra tracker 503 and the track selector 505 in extracting the HR from the optical PPG signal. Thus, the motion signature in FIG. 5 may be used by the system 500 to determine the current activity of the user. In other embodiments, the processor 110 may use a technique similar to that of the activity identifier 504 in determining the type of an exercise, as discussed in greater detail below.

The blocks illustrated in FIG. 5 are merely examples of components and/or processing modules that may be performed to supplement a PPG signal with a motion signature to determine HR. However, in other implementations, the system 500 may include other blocks or may include input from other biometric sensors of the PPG device 100.

Under certain operating conditions, the HR of the user may be measured by counting the number of signal peaks within a time window or by utilizing the fundamental frequency or harmonic frequency components of the signal (e.g., via an FFT). In other cases, such as HR data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signature and the output may be used to perform activity discrimination which may be used to assist the multi-spectra tracker 503. For instance, it may be determined that the user was stationary and has begun to move. This information may be used to by the multi-spectra tracker 503 to bias the track continuation toward increasing frequencies. Similarly, the activity identifier 504 may determine that the user has stopped running or is running slower and this information may be used to preferentially bias the track continuation toward decreasing frequencies.

Tracking may be performed by the multi-spectra tracker 503 with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 505 may use the output tracks from the multiple-spectra tracker 503 and estimate the user's HR based on the output tracks. The track selector 505 may estimate a probability for each of the tracks that the corresponding track is representative of the user's HR. The estimate may be taken as the track having the maximum probability of being representative of the user's HR, a sum of the tracks respectively weighted by their probabilities of being representative of the user's the HR, etc. The activity identifier 504 may determine a current activity being performed by the user which may be used by the track selector 505 in estimating the user's HR. For instance, when the user is sleeping, sitting, lying down, or sedentary, the user's estimated HR may be skewed toward HRs in the 40-80 BPM range. When the user is running, jogging, or doing other vigorous exercise, the user's estimated HR may be skewed toward elevated HRs, such as, for example, in the 90-180 BPM range. The activity identifier 504 may determine the user's current activity (e.g., a current exercise) based at least in part on the speed of the user. The user's estimated HR may be shifted toward (or wholly obtained by) the fundamental frequency of the selected output track when the user is not moving. The output track that corresponds to the user's HR may be selected by the track selector 505 based on criteria that are indicative of changes in activity. For instance, when the user begins to walk from being stationary, the track selector 505 may select the output track that illustrates a shift toward higher frequency based on output received from the activity discriminator 504.

Although some embodiments of the present disclosure are described with respect to HR, the techniques described herein may be extended to other metrics. For example, sensor data generated by the one or more sensors described herein may be used to determine respiration, SpO2, blood volume, blood glucose, skin moisture, and skin pigmentation level and, for example, utilize such metrics for activity detection/identification. Further, the motion removal techniques described in the present disclosure may be used in conjunction with other motion removal techniques.

Removing Motion Component from PPG Signals

Figure 6:
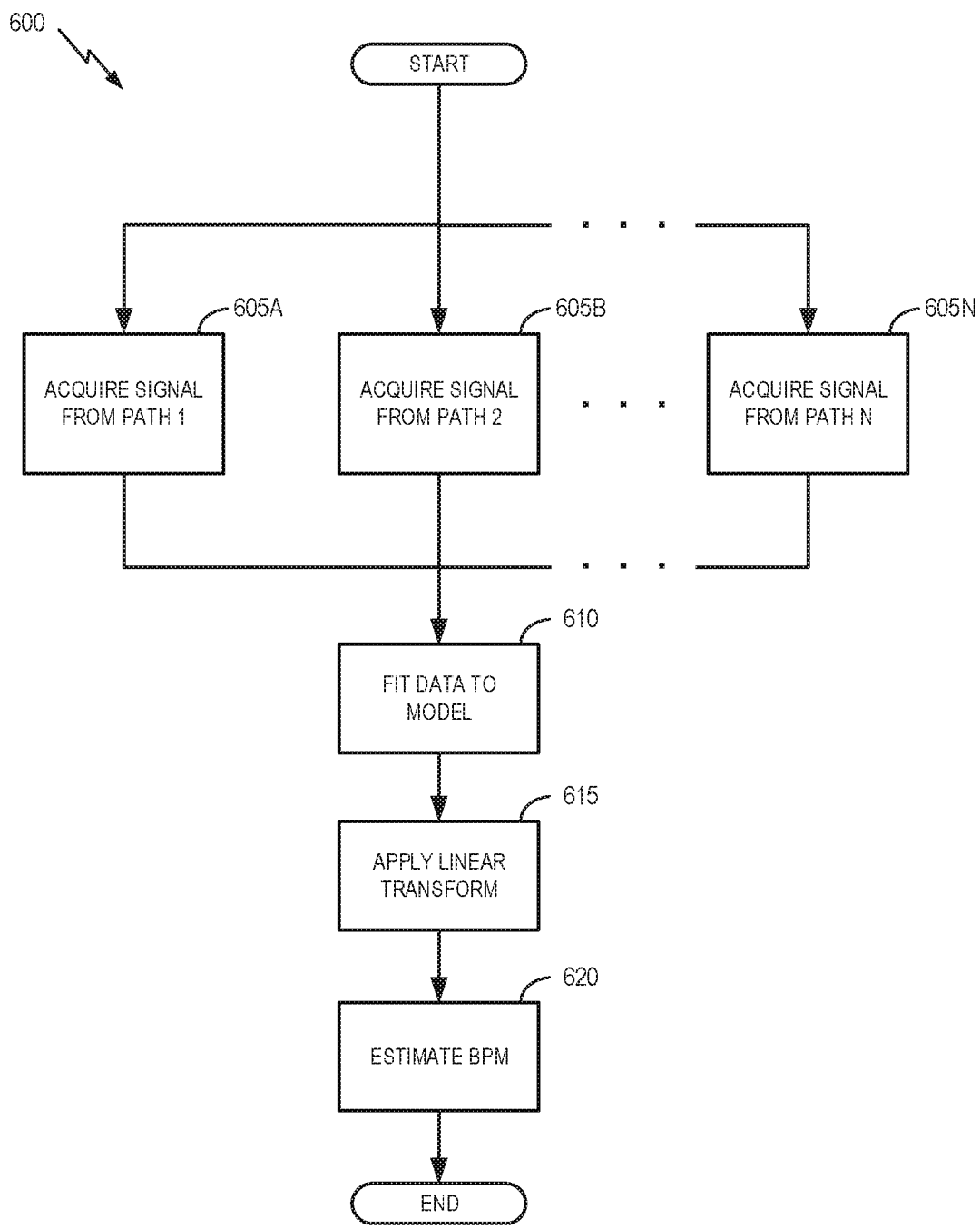
FIG. 6 illustrates another example method of generating a physiological metric using multiple light paths in accordance with aspects of this disclosure.

FIG. 6 illustrates an example method of generating a physiological metric using multiple light paths in accordance with aspects of this disclosure. The method 600 may be operable by a PPG device 100, or component(s) thereof, for generating HR or other physiological metrics in accordance with aspects of this disclosure. For example, the steps of method 600 illustrated in FIG. 6 may be performed by a processor 110 of the PPG device 100. In another example, a user device (e.g., mobile phone) or a server in communication with the PPG device 100 may perform at least some of the steps of the method 600. For convenience, the method 600 is described as being performed by the processor 110 of the PPG device 100.

At block 605A, the processor 110 acquires signal A from path A. At block 605B, the processor 110 acquires signal B from path B. In an embodiment having N unique paths, at block 605N, the processor 110 acquires signal N from path N, where N is a natural number. Although not shown in FIG. 6, there may be any number of similar acquisition steps between blocks 605B and 605N for each unique path.

At block 610, the processor 110 fits the data to a model. For example, the processor 110 may determine whether the PPG signals can be fitted to one of the mathematical models stored on the PPG device 100 to isolate the cardiac component (or any other physiological component) from the motion component.

At block 615, the processor 110 applies a linear transform. For example, the processor 110 may apply a linear transform to the motion component identified at block 610 before subtracting the motion component from the composite PPG signals (e.g., signals including both cardiac and motion components, or signals including the motion component and another physiological component). Other correction techniques may include ICA and other forms of blind source separation.

At block 620, the processor 110 estimates a BPM. For example, the processor 110 may estimate the BPM based on the resulting PPG signal from which the motion component has been removed at block 615.

In the method 600, one or more of the blocks shown in FIG. 6 may be removed (e.g., not performed) and/or the order in which the method is performed may be switched. In some embodiments, additional blocks may be added to the method 600. The embodiments of the present disclosure are not limited to or by the example shown in FIG. 6, and other variations may be implemented without departing from the spirit of this disclosure.

Selecting Best PPG Signal

Figure 7:
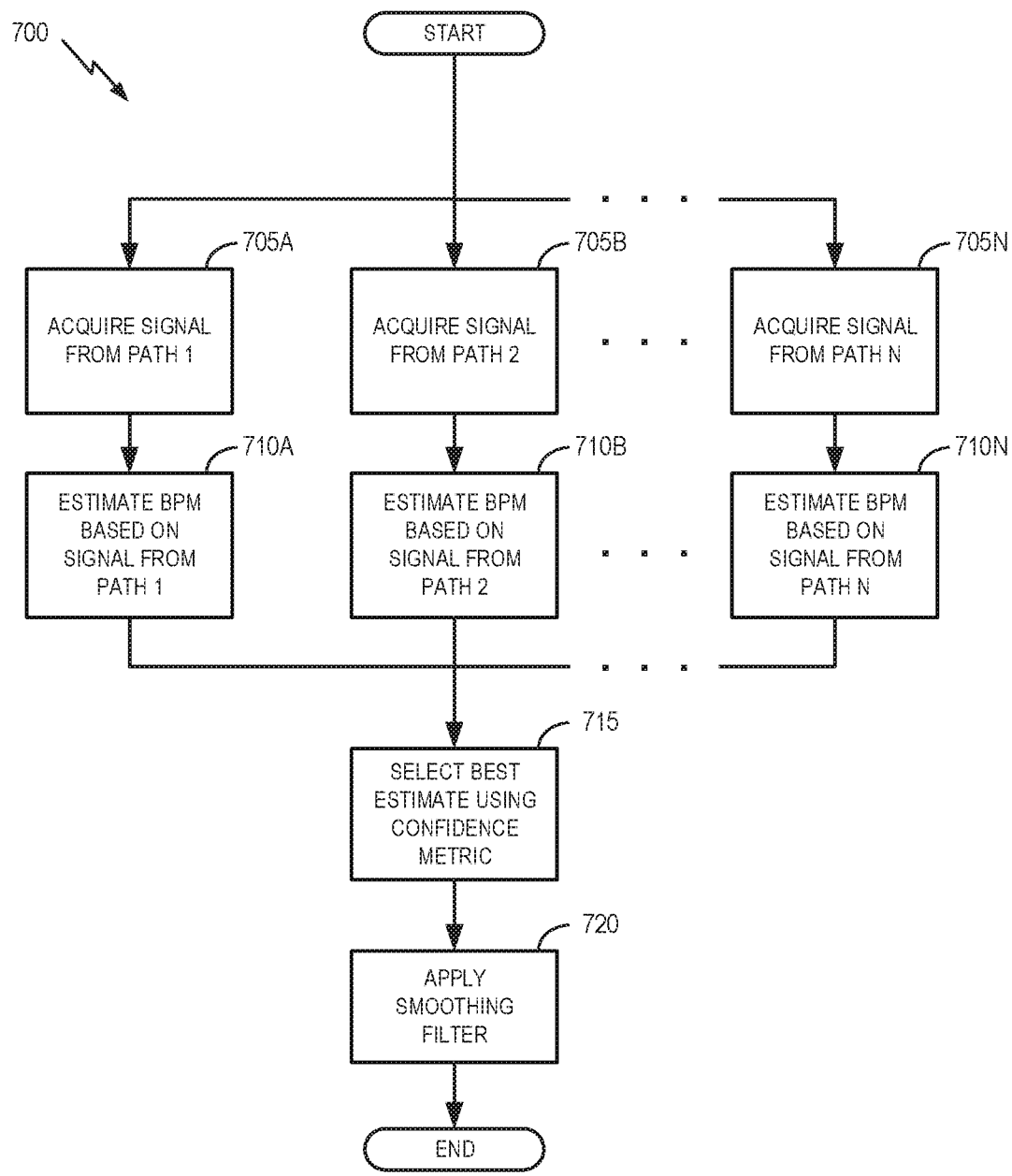
FIG. 7 illustrates another example method of generating a physiological metric using multiple light paths in accordance with aspects of this disclosure.

FIG. 7 illustrates an example method of generating a physiological metric using multiple light paths in accordance with aspects of this disclosure. The method 700 may be operable by a PPG device 100, or component(s) thereof, for generating HR or other physiological metrics in accordance with aspects of this disclosure. For example, the steps of method 700 illustrated in FIG. 7 may be performed by a processor 110 of the PPG device 100. In another example, a user device (e.g., mobile phone) or a server in communication with the PPG device 100 may perform at least some of the steps of the method 700. For convenience, the method 700 is described as being performed by the processor 110 of the PPG device 100.

At block 705A, the processor 110 acquires signal A from path A. At block 705B, the processor 110 acquires signal B from path B. In an embodiment having N unique paths, at block 705N, the processor 110 acquires signal N from path N, where N is a natural number. Although not shown in FIG. 7, there may be any number of similar acquisition steps between blocks 705B and 705N for each unique path.

At block 710A, the processor 110 estimates a BPM based on signal A. At block 710B, the processor 110 estimates a BPM based on signal B. In an embodiment having N unique paths, at block 710N, the processor 110 estimates a BPM based on signal N, where N is a natural number. Although not shown in FIG. 7, there may be any number of similar estimation steps between blocks 710B and 710N for each unique path.

At block 715, the processor 110 selects the best BPM estimate using a confidence metric. For example, the processor 110 compares the PPG signals corresponding to multiple light paths using a confidence/quality metric such as SNR and selects the PPG signal having the highest confidence/quality to be used for estimating the HR of the user. In one embodiment, the processor 110 selects one estimate, among those obtained via blocks 710A-710N, that has the highest confidence metric (e.g., SNR). In some embodiments, the confidence/quality metric is based on the characteristics of the waveform (e.g., waveform feature, waveform fidelity, etc.). In an embodiment, the method 700 may use hysteresis logic that prevents jumping between PPG signals of two different light paths within a short time window, for example, if the confidence values of both are within a specified tolerance value.

In another embodiment, the processor 110 selects a BPM estimate based on an activity-specific confidence metric. For example, if the user is determined to be running, the processor 110 may calculate a running-specific confidence metric for each BPM estimate and select a BPM estimate based on the individual running-specific confidence metric values. As another example, if the user is determined to be sitting, the processor 110 may calculate a sitting-specific confidence metric for each BPM estimate and select a BPM estimate based on the individual sitting-specific confidence metric values. In yet another example, if the user is determined to be sleeping, the processor 110 may calculate a sleeping-specific confidence metric for each BPM estimate and select a BPM estimate based on the individual sleeping-specific confidence metric values. The processor 110 may perform activity detection according to any known activity detection techniques.

At block 720, the processor 110 applies a smoothing filter. For example, the processor 110 may apply the smoothing filter to smooth the estimated HR value. Filtering can be performed to improve accuracy, or to present a better user experience, or for both.

In the method 700, one or more of the blocks shown in FIG. 7 may be removed (e.g., not performed) and/or the order in which the method is performed may be switched. In some embodiments, additional blocks may be added to the method 700. The embodiments of the present disclosure are not limited to or by the example shown in FIG. 7, and other variations may be implemented without departing from the spirit of this disclosure.

Physiological Metrics Based On Machine Learning

In some embodiments, the processor 110 processes multiple PPG signals. For example, each PPG signal of the multiple PPG signals may represent a unique source-detector pair (e.g., light source A to light detector X). The signal quality of the multiple PPG signals may vary depending on a variety of factors (time, location on the user's wrist, weather, orientation of the device, how tightly the user is wearing the device, magnitude and/or direction of movement experienced by the device, activity being performed by the user, and the like). Thus, the processor 110 may determine which one or ones of the multiple PPG signals may more accurately represent the various physiological metrics of the user such that the resulting value is more accurate than that resulting from relying on a single source-detector pair regardless of the changes in the various factors discussed above.

In some embodiments, machine learning can be used to update or optimize the way that the processor 110 processes the multiple PPG signals to generate a value for the physiological parameters. For example, the processor 110 may access a set of PPG signals and determine, using a signal analysis engine stored in one or more memories of the wearable device (e.g., memory 112), whether the accessed set of PPG signals requires updating weight values corresponding to the individual signals in the set. The signal analysis engine can be trained, using unsupervised learning (e.g., in some cases, further based on motion data from the accelerometer and/or previously done supervised learning), to update the weight values based on one or more metrics (e.g., confidence values) associated with the individual signals in the set or other environmental factors (e.g., time, location on the user's wrist, weather, orientation of the device, how tightly the user is wearing the device, magnitude and/or direction of movement experienced by the device, activity being performed by the user, and the like). For example, the processor 110 may determine the final value to be outputted on the graphical user interface based on the PPG signal (or an estimated value based on the PPG signal) with the highest confidence value. In some cases, some or all of the PPG signals (e.g., two or more PPG signals with the highest confidence values, or two or more estimates with the highest confidence values) may be averaged or weighted for the purpose of determining the final value.

The processor 110 may be notified (e.g., by a motion sensor of the wearable device) of movements undergone by the wearable device. For example, the motion sensor may be an accelerometer configured to generate motion data indicative of the movements undergone by the wearable device. The processor 110 may output a final value of the physiological metric tracked by the wearable device based at least on the updated weight values. The final value may be displayed on a display of the wearable device.

In some embodiments, the confidence values (associated with the individual PPG signals or estimates generated therefrom), the final values of the physiological metrics, the identity of the PPG signals (or source-detector paths) used for generating the final values, and/or the weights corresponding to the individual PPG signals (or source-detector paths), or any combination thereof, can serve as a training data set for updating or improving (e.g., by adjusting the individual weights) the way in which the processor 110 determines the final values of the physiological metrics. For example, if the confidence values associated with a given source-detector path exhibit a pattern of being lower than a threshold value when there is user motion along a given rotational axis, the weight value associated with given source-detector path may be reduced when the processor 110 detects user motion along the given rotational axis. As another example, if the confidence values associated with a given source-detector path exhibit a pattern of being higher than a threshold value regardless of environmental conditions, the weight value associated with given source-detector path may be increased for all environmental conditions.

Combining PPG Signals

In some embodiments, at least some of the PPG signals are averaged together to produce a single PPG signal. For example, two of the three PPG signals corresponding to the three unique light paths are averaged together to produce a single PPG signal. Then, the PPG device 100 may generate HR, SpO2, and/or other physiological metrics based on the averaged PPG signal and the remaining one of the three PPG signal. For example, in some cases, the light detector can be a camera sensor consisting of millions of pixels or individual detectors. Since performing a BPM estimation on millions of individual pixels may be difficult, the PPG device 100 may combine the signals received at some of the pixel locations by averaging such pixel signals together, and performing the BPM estimation on the fewer number of signals. In some implementations, even with the averaging of at least some of the PPG signals, the number of signals based on which the PPG device 100 generates the HR, SpO2, and/or other physiological metrics is greater than 1. In other embodiments, none of the PPG signals are averaged together (i.e., each PPG signal is separately considered by the PPG device 100).

Adaptive Activation of Sensors

Additionally or alternatively, the processes of FIGS. 3, 4, 6, and 7 may utilize input from biometric sensors or environmental sensors indicating an ambient temperature or a skin temperature of the wearer of the activity monitoring apparatus. Based on changes in temperature values received from these sensors, the process may energize or de-energize different arrangements of light sources 102. In this embodiment, the processes of FIGS. 3, 4, 6, and 7 may further include: activating only a first set of light sources and deactivating all other light sources; receiving, at the one or more light detectors of the PPG device, first PPG signals from only the first set of light sources; receiving an ambient temperature signal from an ambient temperature sensor that is located proximate to the first set of light sources; determining that the ambient temperature signal is less than a stored minimum temperature signal; based on the determination, activating a second set of light sources; receiving, at the one or more light detectors of the PPG device, second PPG signals from the second set of light sources; combining at least some of the first and second PPG signals; and generating HR, SpO2, and/or other physiological metrics based on the combined signals. Although the ambient temperature is used as an example, the selective activation of light sources can be extended to other sensor data. Further, light detectors can also be selectively activated based on sensor data obtained by the PPG device.

In some embodiments, one or more light paths are selectively activated based on the user activity. For example, if it is determined that the user is currently sleeping, only a low number of light paths may be activated (e.g., 1 or 2), if it is determined that the user is currently walking, a higher number of light paths may be activated (e.g., 3 or 4), and if it is determined that the user is currently engaging in a high intensity exercise (e.g. running), an even higher number of light paths may be activated (e.g., 5 or 6). Alternatively, in some embodiments, different activities may result in activation of different but the same number of light paths. For example, if it is determined that the user is currently sleeping, only light paths A and B may be activated, if it is determined that the user is currently walking, only light paths C and D may be activated, and if it is determined that the user is currently engaging in an exercise, only light paths E and F may be activated. In other embodiments, the number and the identity of light paths may both vary depending on the detected activity. For example, if it is determined that the user is currently sleeping, only light path A may be activated, if it is determined that the user is currently walking, only light paths B and C may be activated, and if it is determined that the user is currently engaging in an exercise, only light paths D, E, and F may be activated. Such embodiments allow activity-specific arrangement of light sources and detectors to be used, such that the signal-to-noise ratio is improved or optimized. Although described in the activity detection context, these techniques can be extended to movement detection to provide movement-state-specific (e.g., based on whether the device is undergoing no movement, movement less than a threshold, moving greater than a threshold value, etc.) arrangement of light sources and detectors.

As discussed above, one of the advantages in some of the embodiments described herein is that the spatial information associated with the light sources and/or light detectors can be used by different algorithms to improve estimation accuracy of the PPG sensing device for HR, SpO2, and/or other physiological metrics, especially when the user of the device is exercising or performing activities involving motion. Existing implementations typically rely on algorithms to improve the estimation performance for HR, SpO2, and/or other physiological metrics, but do not have the benefit of the extra sensor data generated based on multiple light paths.

Example Embodiments (EEs)

EE 1. A method for generating physiological metrics, the method comprising: obtaining one or more first PPG signals based on light received by a first light detector from a set of light sources, each light source in the set (i) having a spatial location that is different from that of another light source in the set and (ii) configured to emit light according to an emission schedule that is different from that of another light source in the set; obtaining one or more second PPG signals based on light received by a second light detector from the set of light sources; generating a physiological metric based on one or more of the first and second PPG signals; and causing the physiological metric to be displayed via a user interface on a user device.

EE 2. The method of EE 1, wherein the set of light sources comprises at least one green light source, at least one red light source, and at least one infrared light source.

EE 3. The method of EE 1, wherein the set of light sources are provided across two or more light source packages, each light source package including at least one light source from the set and located at least 1 mm away from another one of the two or more light source packages.

EE 4. The method of EE 1, wherein the set of light sources comprises two or more light sources included in a single light source package, wherein the two or more light sources in the light source package are each configured to emit light having a wavelength that is different from another light source in the light source package.

EE 5. The method of EE 4, wherein the two or more light sources in the light source package are located within less than 1 mm from each other.

EE 6. The method of EE 5, wherein the two or more light sources comprise at least a red light source and an infrared light source.

EE 7. The method of EE 1, further comprising: obtaining a first signal of the one or more first PPG signals based on the light received by the first light detector from a first light source in the set during a first temporal window; obtaining a second signal of the one or more first PPG signals based on the light received by the first light detector from a second light source in the set that is different from the first light source during a second temporal window that is different from the first temporal window; and generating the physiological metric based at least on the first signal and the second signal.

EE 8. The method of EE 7, further comprising removing a motion component from at least one of the first and second signals based on location information associated with one or more of the first light source, the second light source, and the first light detector.

EE 9. The method of EE 7, further comprising: determining a first confidence metric associated with the first signal; determining a second confidence metric associated with the second signal; and based on a determination that the first confidence metric is higher than the second confidence metric, generating the physiological metric based on the first signal.

EE 10. The method of EE 1, further comprising: obtaining a first signal of the one or more first PPG signals based on the light received by the first light detector from a first light source in the set; obtaining a second signal of the one or more second PPG signals based on the light received by the second light detector from the first light source in the set; and generating the physiological metric based at least on the first signal and the second signal.

EE 11. The method of EE 10, further comprising removing a motion component from at least one of the first and second signals based on location information associated with one or more of the first light source, the first light detector, and the second light detector.

EE 12. The method of EE 10, further comprising: determining a first confidence metric associated with the first signal; determining a second confidence metric associated with the second signal; and based on a determination that the first confidence metric is higher than the second confidence metric, generating the physiological metric based on the first signal.

EE 13. The method of EE 1, wherein the first and second light sources are spatially located between the first and second light detectors.

EE 14. The method of EE 1, wherein the first and second light detectors are spatially located between the first and second light sources.

EE 15. The method of EE 1, wherein the first and second light sources and the first and second light detectors are arranged such that each of the set of light sources is equidistant from the first and second light detectors.

EE 16. A wearable device for tracking a physiological metric of a user, comprising: two or more light emitters that are each configured to emit light at a respective emission schedule; a first light sensor positioned at a first location on the wearable device and configured to receive light from the two or more light emitters; a second light sensor positioned at a second location on the wearable device different from the first location and configured to receive light from the two or more light emitters; and an element configured to receive signals generated by the first and second light sensors and determine a value of the physiological metric associated with the user of the wearable device based on the received signals.

EE 17. The wearable device of EE 16, wherein the first light sensor is configured to receive light along a first rotational axis of the wearable device, and the second light sensor is configured to receive light along a second rotational axis of the wearable device different from the first rotational axis.

EE 18. The wearable device of EE 16, wherein the element is further configured to: receive a first signal based on light received by the first light sensor from a first light emitter of the two or more light emitters during a first temporal window; receive a second signal based on light received by the first light sensor from a second light emitter of the two or more light emitters that is different from the first light emitter during a second temporal window that is different from the first temporal window; and generate the value of the physiological metric based at least on the first signal and the second signal.

EE 19. The wearable device of EE 16, wherein the element is further configured to: receive a first signal based on light received by the first light sensor from a first light emitter of the two or more light emitters; receive a second signal based on light received by the second light sensor from the first light emitter; and generate the value of the physiological metric based at least on the first signal and the second signal.

EE 20. A method comprising: accessing, at a wearable device for tracking a physiological metric, a set of PPG signals; determining, using a signal analysis engine stored in one or more memories of the wearable device, whether the accessed set of PPG signals requires updating weight values corresponding to the individual signals in the set, the signal analysis engine being trained, using unsupervised learning, to update the weight values based on one or more environmental factors and being notified, via a motion sensor of the wearable device, of movements undergone by the wearable device, the motion sensor configured to generate motion data indicative of the movements undergone by the wearable device; and outputting, based at least on the updated weight values, a value of the physiological metric associated with a user of the wearable device on a display of the wearable device.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

According to some embodiments, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices, wearable devices, or any other device that incorporates hard-wired and/or program logic to implement the techniques.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, FPGAs, or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure.

What is claimed is:

1. A method for generating a heart rate estimation, the method. comprising:
obtaining a first PPG signal based on light received by a light detector from a first light source during a first temporal window during which a second light source is not emitting light;

obtaining a second PPG signal based on light received by the light detector from the second light source different from the first light source and during a second temporal window that is different from the first temporal window and during which the first light source is not emitting light;

processing the first and second PPG signals using one or more machine learning algorithms to remove a motion component from the first and second PPG signals;

determining the heart rate estimation in beats-per-minute using the processed first and second PPG signals having the motion component removed therefrom; and causing the heart rate estimation to be displayed via a user interface on a user device.

2. The method of claim 1, wherein the one or more machine learning algorithms comprises at least one of previously-completed supervised machine learning or unsupervised machine learning.

3. The method of claim 1, further comprising:
determining at least one confidence metric associated with at least one of the first and second PPG signals, the confidence metric being indicative of a signal quality for a particular light path associated with each of the first and second PPG signals; and
determining the heart rate estimation in beats-per-minute using the processed first and second PPG signals and the at least one confidence metric.

4. The method of claim 3, further comprising processing the at least one confidence metric associated with at least one of the first and second PPG signals using the one or more machine learning algorithms.

5. The method of claim 4, wherein the one or more machine learning algorithms comprise unsupervised machine learning.

6. The method of claim 3, further comprising:
determining an intermediate heat rate estimation based on the first and second PPG signals; and
determining the heart rate estimation in beats-per-minute using the intermediate heat rate estimation and the at least one confidence metric associated with at least one of the first and second PPG signals.

7. The method of claim 3, further comprising:
characterizing characteristics of the first and second PPG signals or filtered versions of the first and second PPG signals; and
determining the heart rate estimation in beats-per-minute using at least one of the characteristics or the filtered versions of the first and second PPG signals and the at least one confidence metric associated with at least one of the first and second PPG signals.

8. The method of claim 3, wherein the at least one confidence metric associated with at least one of the first and second PPG signals corresponds to only one of the first or second PPG signals.

9. The method of claim 3, wherein the at least one confidence metric associated with at least one of the first and second PPG signals corresponds to both of the first and second PPG signals.

10. The method of claim 3, wherein determining the heart rate estimation in beats-per-minute using the processed first and second PPG signals and the at least one confidence metric further comprises selecting the heart rate estimation corresponding to the first PPG signal or the second PPG signal having a higher confidence metric.

11. The method of claim 1, further comprising implementing logic configured to bias the determination of the heart rate estimation based on at least one of user data, activity data, or movement data.

12. The method of claim 1, further comprising implementing hysteresis logic to prevent jumping between light paths in a short time window at least one confidence metric corresponds to light paths within a threshold value.

13. A wearable device for tracking a heart rate estimation of a user, comprising:
a first light source;
a second light source different from the first light source;
a light detector;
a memory; and
one or more processors, wherein the memory stores computer-executable instructions for causing the one or more processors to:
obtain a first PPG signal based on light received by the light detector from the first light source during a first temporal window in which the second light source is not emitting light,
obtain a second PPG signal based on light received by the light detector from the second light source during a second temporal window that is different from the first temporal window and during which the first light source is not emitting light,
process the first and second PPG signals using one or more machine learning algorithms;
determine the heart rate estimation in beats-per-minute using the processed first and second PPG signals; and
cause the heart rate estimation to be displayed via a user interface on a user device.

14. The wearable device of claim 13, wherein the one or more machine learning algorithms comprises at least one of previously-completed supervised machine learning or unsupervised machine learning.

15. The wearable device of claim 13, wherein the computer-executable instructions further cause the one or more processors to:
determine at least one confidence metric associated with at least one of the first and second PPG signals, the confidence metric being indicative of a signal quality for a particular light path associated with each of the first and second PPG signals; and
determine the heart rate estimation in beats-per-minute using the processed first and second PPG signals and the at least one confidence metric.

16. The wearable device of claim 15, wherein the computer-executable instructions further cause the one or more processors to:
process the at least one confidence metric associated with at least one of the first and second PPG signals using the one or more machine learning algorithms.

17. The wearable device of claim 15, wherein the computer-executable instructions further cause the one or more processors to:
determine an intermediate heat rate estimation based on the first and second PPG signals; and
determine the heart rate estimation in beats-per-minute using the intermediate heat rate estimation and the at least one confidence metric associated with at least one of the first and second PPG signals.

18. The wearable device of claim 15, wherein the computer-executable instructions further cause the one or more processors to:
characterize characteristics of the first and second PPG signals or filtered versions of the first and second PPG signals; and determine the heart rate estimation in beats-per-minute using at least one of the characteristics or the filtered versions of the first and second PPG signals and the at least one confidence metric associated with at least one of the first and second PPG signals.

19. The wearable device of claim 15, wherein the at least one confidence metric associated with at least one of the first and second PPG signals corresponds to one of the first PPG or the second PPG signal.

20. The wearable device of claim 15, wherein the at least one confidence metric associated with at least one of the first and second PPG signals corresponds to both of the first and second PPG signals.

* * * * *